US008554316B2

(12) United States Patent
Shimizu et al.

(10) Patent No.: US 8,554,316 B2
(45) Date of Patent: Oct. 8, 2013

(54) BIOLOGICAL INFORMATION MEASUREMENT DEVICE, BIOLOGICAL INFORMATION MEASUREMENT METHOD, AND BODY COMPOSITION MEASUREMENT DEVICE

(75) Inventors: Satoe Shimizu, Kyoto (JP); Naoto Mukai, Kyoto (JP); Yasuo Fujita, Nagaokakyo (JP)

(73) Assignee: Omron Healthcare Co., Ltd., Kyoto (JP)

( * ) Notice: Subject to any disclaimer, the term of this patent is extended or adjusted under 35 U.S.C. 154(b) by 17 days.

(21) Appl. No.: 13/206,160

(22) Filed: Aug. 9, 2011

(65) Prior Publication Data
US 2012/0004570 A1 Jan. 5, 2012

Related U.S. Application Data

(63) Continuation of application No. PCT/JP2010/052523, filed on Feb. 19, 2010.

(30) Foreign Application Priority Data

Feb. 20, 2009 (JP) ................................ 2009-037299

(51) Int. Cl.
*A61B 5/05* (2006.01)
(52) U.S. Cl.
USPC ........................................................ 600/547
(58) Field of Classification Search
USPC .................. 600/300, 547, 587, 595
See application file for complete search history.

(56) References Cited

U.S. PATENT DOCUMENTS

| 6,308,096 | B1 * | 10/2001 | Masuo ........................... 600/547 |
| 6,490,481 | B1 * | 12/2002 | Komatsu et al. ............... 600/547 |
| 7,130,680 | B2 * | 10/2006 | Kodama et al. ................ 600/547 |
| 7,336,992 | B2 * | 2/2008 | Shiokawa ....................... 600/547 |
| 2004/0026037 | A1 | 2/2004 | Shinriki et al. |
| 2009/0131812 | A1 * | 5/2009 | Sato et al. ....................... 600/547 |

FOREIGN PATENT DOCUMENTS

| CN | 101370428 A | 2/2009 |
| JP | A-2002-151489 | 5/2002 |
| JP | A-2004-337578 | 12/2004 |
| JP | A-2006-81601 | 3/2006 |
| WO | WO 02/43586 A1 | 6/2002 |
| WO | WO 2007083563 A1 * | 7/2007 |

OTHER PUBLICATIONS

International Search Report dated May 25, 2010 in International Application No. PCT/JP2010/052523 (with translation).
Apr. 8, 2013 Office Action issued in Chinese Patent Application No. 201080008684.X (with translation).

* cited by examiner

*Primary Examiner* — Max Hindenburg
*Assistant Examiner* — Adam Eiseman
(74) *Attorney, Agent, or Firm* — Oliff & Berridge, PLC

(57) ABSTRACT

To accurately acquire body composition information using data acquired by another device. Thus, there is provided a body composition monitor with scale including a communication unit for allowing input of biological component information (cross-sectional area, site length, subcutaneous fat percentage, visceral fat percentage, etc.) of a living body measured with another device such as an MRI, where step of calculating the body composition of the living body based on the biological component information, an impedance detected by an impedance detection unit, and a weight measured by a load detection unit is executed.

8 Claims, 14 Drawing Sheets

| Variable name | Input method |
|---|---|
| Height | Manual input in advance |
| Sex | Manual input in advance |
| Age | Manual input in advance |
| Weight | Measurement each time |
| Impedance | Measurement each time |

11

(B)

| Variable name | Input method |
|---|---|
| Cross-sectional area | Register in advance |
| Site length | Register in advance |
| Weight | Measurement each time |
| Impedance | Measurement each time |

12

(C)

| Variable name | Input method |
|---|---|
| Body fat percentage | Measurement each time |
| Weight | Measurement each time |

13

(D)

| Variable name | Input method |
|---|---|
| Subcutaneous fat percentage | Register in advance |
| Visceral fat percentage | Register in advance |
| Body fat percentage | Measurement each time |
| Weight | Measurement each time |

14

Fig. 12
(A)
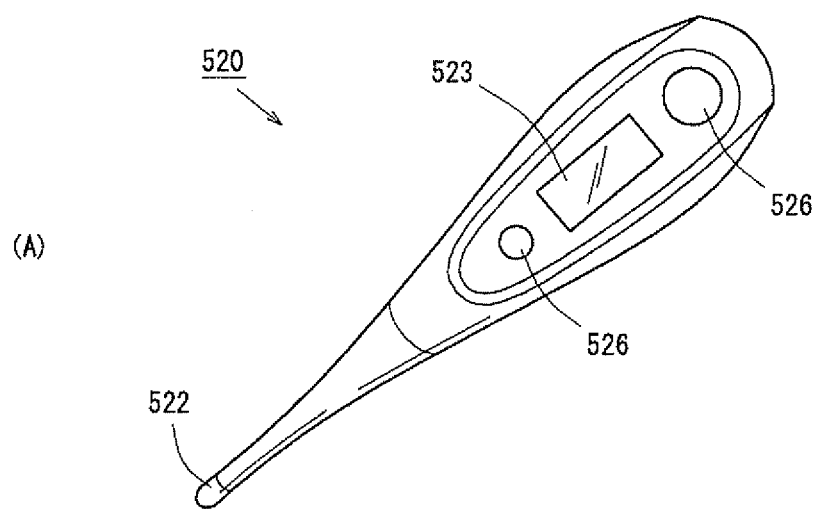
(B)
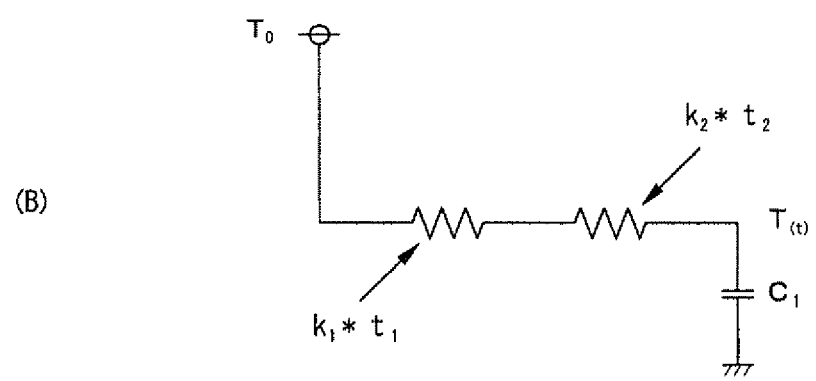

BIOLOGICAL INFORMATION MEASUREMENT DEVICE, BIOLOGICAL INFORMATION MEASUREMENT METHOD, AND BODY COMPOSITION MEASUREMENT DEVICE

TECHNICAL FIELD

The present invention relates to a biological information measurement device, a biological information measurement method, and a body composition measurement device for acquiring biological information of a living body, for example.

BACKGROUND ART

A device for measuring various biological information is conventionally known. As a device for measuring the biological information, for example in a body composition measurement device, a method of measuring the impedance of a body to calculate a body composition value from the difference in electrical characteristics of the fat and the muscle is known for an estimating method of a body fat percentage, a subcutaneous fat percentage, or the like. The estimation equation of the body composition is calculated from a correlation of the measurement data from, for example, MRI, CT scan, and DEXA of a great number of subjects, and the impedance value.

As such, there is proposed a method of estimating the body composition such as muscle amount from the measurement value of the impedance using the estimation equation created by a regression analysis based on the data collected in advance with the MRI (see Patent Document 1).

However, the estimation error may occur since the electrical characteristics differ among people in some degree. In particular, the estimation error tends to become large in children and athletes.

Patent Document 1: International Patent Publication 2002/43586

SUMMARY OF THE INVENTION

Problems to be Solved by the Invention

In view of the above problems, it is an object of the present invention to provide a biological information measurement device, a biological information measurement method, and a body composition measurement device for accurately acquiring the biological information using the data acquired by other devices, and to enhance the satisfaction level of the user.

Means for Solving the Problems

The present invention relates to a biological information measurement device including measurement means for acquiring measurement value information of a living body; and calculation means for calculating biological information based on measurement value information obtained by the measurement means; the biological information measurement device further including input means for inputting biological component information about a component of the living body measured in another device, in which the calculation means is configured to execute a biological component reflecting calculation process of calculating the biological information based on the biological component information and the measurement value information, and a correction calculation method determining process of obtaining a correction calculation method dedicated to the living body based on the biological component information and the impedance of the living body measured within a predetermined period from a measurement date and time of the biological component information, and to change whether or not to adopt the correction calculation method in the biological component reflecting calculation process based on measurement date and time of the biological component information and change in body composition from the measurement date and time to present.

Another device is an appropriate device that acquires the body composition component information such as an MRI (Magnetic Resonance Imaging), CT (Computed Tomography), and DEXA (Dual Energy X-Ray Absorptiometry).

The biological component information is appropriate information about a biological component such as a cross-sectional area, a site length, a subcutaneous fat percentage, a visceral fat percentage, a contact impedance of the skin, or pluralities of the same.

According to the present invention, the biological information can be accurately acquired using data acquired by another device.

The body composition can be prevented from being calculated using old biological component information.

Furthermore, even the old biological component information can be used without any problem if there is no change in body composition, whereas even relatively new biological component information is not used if the change in body composition is rapid, so that a more appropriate body composition measurement can be executed.

The present invention also relates to a body composition measurement device used as the biological information measurement device, where the measurement value information is an impedance or a weight of a living body; and the biological information is a body composition.

The body composition estimation algorithm can be optimized in accordance with each person by looking at the correlation between the body fat percentage and the visceral fat measured by an MRI (Magnetic Resonance Imaging), CT (Computed Tomography), DEXA (Dual Energy X-Ray Absorptiometry), or the like in hospitals and the like, and the impedance value measured with the body composition monitor. The error that occurs as the electrical characteristics more or less differ among people can be reduced in the body composition estimation using the impedance value.

When using the contact impedance of the skin, the body composition measured with the body composition monitor can be corrected using the contact impedance of the skin measured in hospitals, and the like. Therefore, the accuracy of the body composition measured by the body composition monitor can be enhanced.

In another aspect of the present invention, storage means for storing a living body categorized body composition calculation method categorized by at least one or more conditions of height, age, or sex of the living body is further arranged; and the calculation means executes the biological component reflecting calculation process when the biological component information is acquired, and acquires at least one or more of the height, the age, or the sex of the living body to execute a general body composition calculation process of calculating a body composition using the living body categorized body composition calculation method corresponding to the acquired information when the biological component reflecting calculation process is not acquired.

The living body categorized body composition calculation method is a method in which the constant to be used for the body composition estimation is differed depending on the living body category by height, sex, age, or the like, and the body composition is calculated from the impedance using an appropriate constant.

Therefore, the accurate body composition measurement using the biological component information of the living body and the general body composition measurement using the living body categorized body composition calculation method can be automatically switched and executed.

In still another aspect of the present invention, target information creating means for creating target information about the body composition based on the body composition information is further arranged, in which the target information creating means is configured to correct the target information based on the biological component information.

Therefore, more appropriate target information can be created when the biological component information exists.

The present invention relates to a biological information measurement method for measuring biological information, including measurement means for acquiring measurement value information of a living body and calculation means for calculating biological information based on the measurement value information obtained by the measurement means, the biological information measurement method including the step of allowing input of biological component information about a component of the living body measured in another device by input means, and causing the calculation means to execute a biological component reflecting calculation process of calculating the biological information based on the biological component information and the measurement value information and a correction calculation method determining process of obtaining a correction calculation method dedicated to the living body based on the biological component information and the impedance of the living body measured within a predetermined period from a measurement date and time of the biological component information, and to change whether or not to adopt the correction calculation method in the biological component reflecting calculation process based on measurement date and time of the biological component information and change in body composition from the measurement date and time to present.

With this method, the biological information can be accurately acquired using the data acquired by another device.

The present invention relates to a biological information display method including a selection step of displaying a selection screen for selecting whether or not to input biological component information measured by another device; a step of acquiring measurement value information of a living body; a measurement step of measuring biological information; a biological component reflecting calculation process step of calculating the biological information based on the living body component information and the measurement value information; a correction calculation method determining process step obtaining a correction calculation method dedicated to the living body based on the biological component information and the impedance of the living body measured within a predetermined period from a measurement date and time of the biological component information; a step of changing whether or not to adopt the correction calculation method in the biological component reflecting calculation process based on measurement date and time of the biological component information and change in body composition from the measurement date and time to present; and a display step of displaying whether or not the biological component information is used with the measured biological information.

With this method, the user can easily check whether the measurement result reflects the biological component information or does not reflect the biological component information.

The present invention further relates to a biological information display device including selection means for displaying a selection screen for selecting whether or not to input biological component information measured by another device; measurement means for acquiring measurement value information of a living body; measurement means for measuring biological information; calculation means for executing a biological component reflecting calculation process of calculating the biological information based on the biological component information and the measurement value information, and a correction calculation method determining process of obtaining a correction calculation method dedicated to the living body based on the biological component information and the impedance of the living body measured within a predetermined period from a measurement date and time of the biological component information, and changing whether or not to adopt the correction calculation method in the biological component reflecting calculation process based on measurement date and time of the biological component information and change in body composition from the measurement date and time to present; and display means for displaying whether or not the biological component information is used with the measured biological information.

With this device, the user can easily check whether the measurement result reflects the biological component information or does not reflect the biological component information.

Effects of the Invention

According to the present invention, the biological information can be accurately acquired using the data acquired by another device, and the satisfaction level of the user can be enhanced.

BRIEF DESCRIPTION OF THE DRAWINGS

FIG. 3 is an explanatory diagram describing a configuration of various types of data stored in a storage unit of the first embodiment.

FIG. 12 is an explanatory view of an outer appearance and a heat conduction model of an electronic thermometer according to a fourth embodiment.

MODE FOR CARRYING OUT THE INVENTION

The present invention relates to a body composition monitor for measuring an impedance of a living body and calculating a body composition of the living body, where if there is an actual measurement data obtained from an external device such as an MRI device for the living body, such actual measurement data is used to create an individual calculation equation for the relevant living body, and such individual calculation equation is thereafter used to accurately calculate the body composition from the measured impedance.

One embodiment of the present invention will be described below in conjunction with the drawings.

First Embodiment

Figure 1:
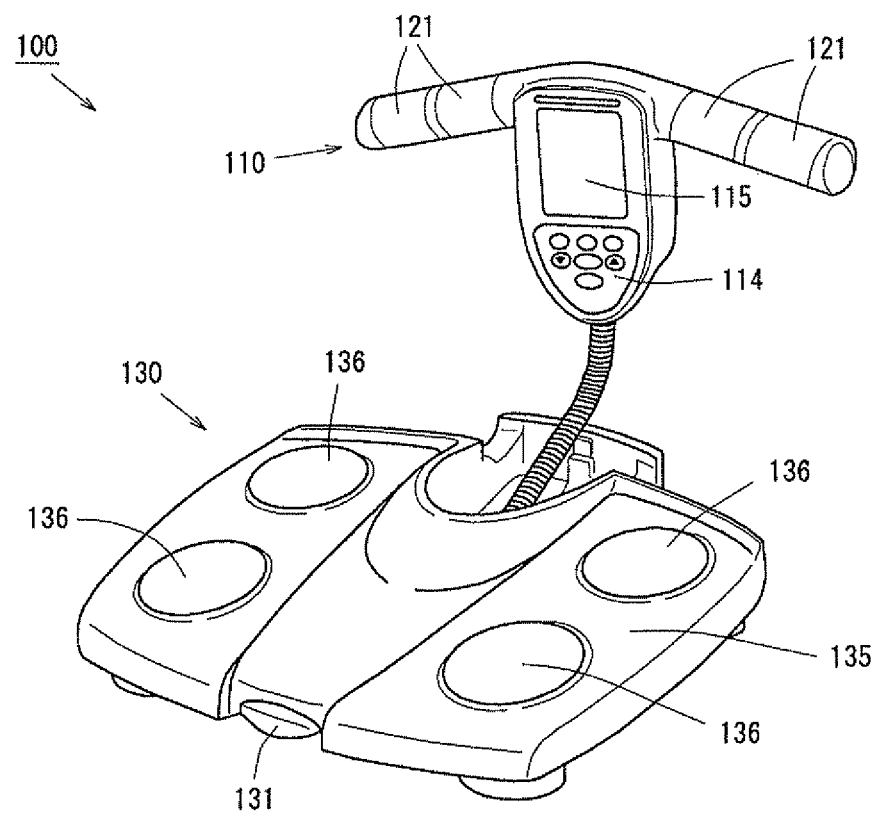
FIG. 1 is a perspective view showing an outer appearance of a body composition monitor with scale of a first embodiment.
Figure 2:
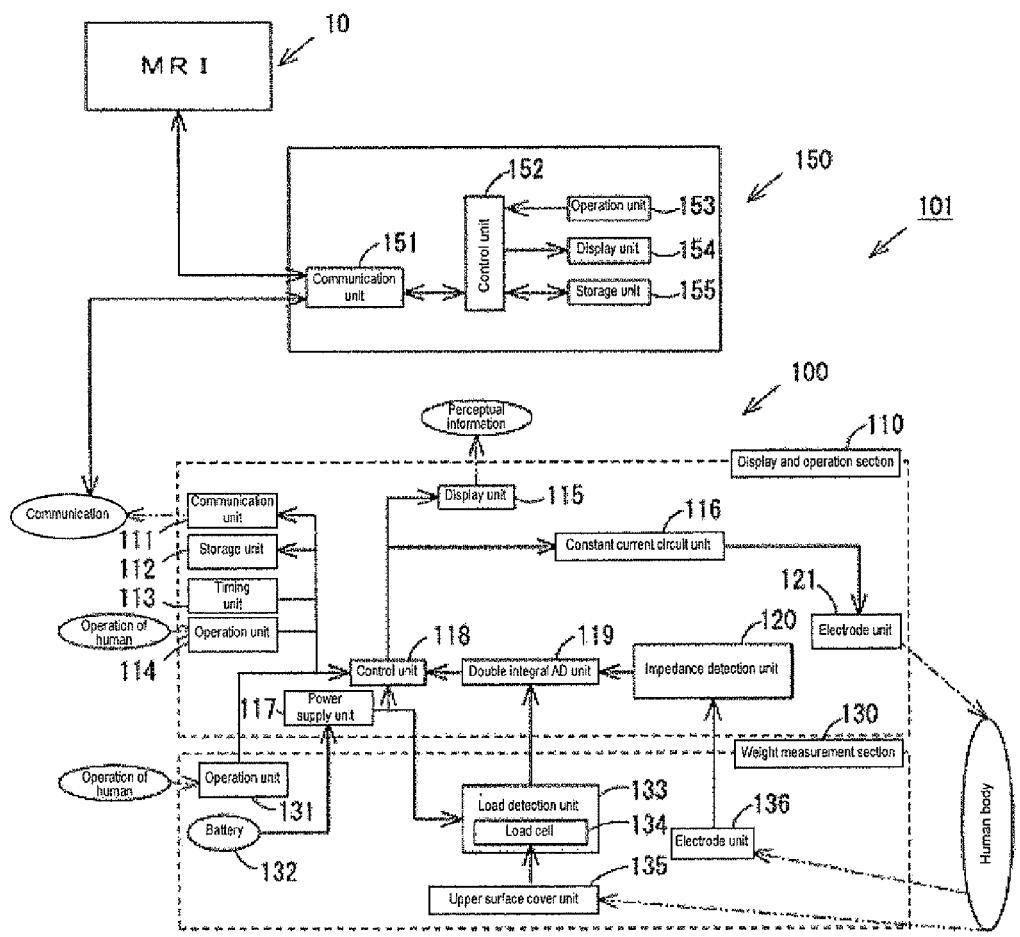
FIG. 2 is a block diagram of a weight management system of the first embodiment.

FIG. 1 is a perspective view showing an outer appearance of a body composition monitor with scale 100, and FIG. 2 is a block diagram showing a configuration of a biological information acquiring system 101 including the body composition monitor with scale 100 and a server 150 capable of communicating with the body composition monitor with scale 100.

As shown in FIG. 1, the body composition monitor with scale 100 mainly includes a display and operation section 110, which is a first housing to be held by a user with hand, and a weight measurement section 130, which is a second housing on which the user goes on, and functions as a body composition monitor and also as a scale.

As shown in FIG. 2, the display and operation section 110 includes a communication unit 111, a storage unit 112, a timing unit 113, an operation unit 114, a display unit 115, a constant current circuit unit 116, a power supply unit 117, a control unit 118, a double integral AD unit 119, an impedance detection unit 120, and an electrode unit 121.

The communication unit 111 is connected to the control unit 118, and communicates with the server 150 according to a control signal of the control unit 118. The communication unit 111 may be configured to communicate not only with the server 150 but also with an appropriate device such as communicate with other biological information acquiring devices including a pedometer or communicate with a personal computer or a personal information terminal (PDA or portable telephone, etc.).

The storage unit 112 includes a device capable of storing information such as nonvolatile memory and hard disk, and carries out read and write of information according to the control signal of the connected control unit 118. The storage unit 112 stores user information on the user. The user information is stored by number such as user 1 and user 2, and stores the sex, the age, and the height of the user or these as well as the weight.

The timing unit 113 (timing means) is a device for timing the time such as the current date and time, and transmits the time to the control unit 118 as needed.

The operation unit 114 includes a plurality of buttons (see FIG. 1) to be push operated, and the input information push operated by the user such as input of physical information of the user including sex, age, height, and weight is transmitted to the control unit 118.

The display unit 115 includes a display device such as a liquid crystal screen (see FIG. 1), and displays characters and figures according to an image signal transmitted from the control unit 118.

The constant current circuit unit 116 flows high frequency (AC) current supplied from the power supply unit 117 in one direction to the electrode unit 121 for current application based on the control of the control unit 118.

The power supply unit 117 supplies the operation power to each unit including the control unit 118.

The control unit 118 includes a CPU, a ROM, a RAM, or a microcomputer, and executes the control operation and the calculation operation of each unit according to a program stored in the ROM, or the like. The body composition measurement program is stored for the program.

The double integral AD unit 119 is a double integral type AD (Analog/Digital) converter, and converts an analog signal provided from the impedance detection unit 120 to a digital signal.

The impedance detection unit 120 detects the impedance of the user based on a potential difference of the electrode unit 136 arranged in the weight measurement section 130 and the electrode unit 121 arranged in the display and operation section 110.

The electrode unit 121 is arranged on the surface of the grip portion (see FIG. 1) of the display and operation section 110 which the user holds with his/her hand, and applies high frequency (AC) current supplied from the power supply unit 117 to the palm of the user gripping the grip portion.

The weight measurement section 130 includes an operation unit 131, a battery 132, a load detection unit 133, and an electrode unit 136.

The operation unit 131 functions as an input switch for switching ON/OFF of the power supply, and transmits the inputted input signal to the control unit 118.

The battery 132 supplies power to each unit with the power supply unit 117 as the center.

The load detection unit 133 incorporates a load cell 134, and measures the weight of the user who got on an upper surface cover unit 135 (see FIG. 1) also serving as an upper surface cover of the housing. The weight measured here is transmitted to the double integral AD unit 119.

The electrode unit 136 is arranged on the surface of the upper surface portion (see FIG. 1) of the weight measurement section 130 on which the user goes on, and is an electrode for current measurement that receives the current flowing from the back of the foot of the user. The electrode unit 136 includes four electrodes; the left toe side, left heel side, right toe side, and right heel side of the user.

The server 150 includes a communication unit 151, a control unit 152, an operation unit 153, a display unit 154, and a storage unit 155.

The communication unit 151 transmits and receives data to and from the body composition monitor with scale 100 according to the control of the control unit 152.

The control unit 152 includes a CPU, a ROM, and a RAM, and executes the control operation and the calculation operation of each unit according to a program stored in the ROM, or the like.

The operation unit 153 includes an operation input device such as a keyboard or a mouse, and transmits the operation inputted input signal to the control unit 152.

The display unit 154 includes a display device such as a liquid crystal display and a CRT display, and displays according to a control signal of the control unit 152.

The storage unit 155 includes a storage device such as a hard disk, and stores various data about the user such as the body composition data (body fat data and weight data) measured with the body composition monitor with scale 100 and personal information such as name and address of the user.

The biological information acquiring system 101 includes the body composition monitor with scale 100 and the server 150 configured as above.

FIG. 3 is an explanatory view describing the configuration of various types of data stored in the storage unit 112.

FIG. 3(A) shows the data configuration of general calculation variable data 11.

The general calculation variable data 11 includes five items: height, sex, age, weight, and impedance.

The height, sex and age are variables manually inputted by the operation unit 114 and registered in advance.

The weight and the impedance are variables measured each time by the load detection unit 133 and the impedance detection unit 120, respectively.

FIG. 3(B) shows the data configuration of specific individual dedicated variable data 12. The specific individual dedicated variable data 12 includes four items of cross-sectional area, site length, weight, and impedance.

The cross-sectional area and the site length have the actual measurement values measured with the MRI, DEXA or the like registered in advance. This pre-registration may be made according to an appropriate method such as registering by receiving the values from the server 150 or an external device such as the MRI 10 through the communication unit 111, or registering by manual input of the values by means of the operation unit 114.

The weight and the impedance are variables measured each time by the load detection unit 133 and the impedance detection unit 120.

FIG. 3(C) shows the data configuration of general target calculation data 13. The general target calculation data 13 includes a body fat percentage and a weight. The body fat percentage and the weight are variables obtained each time by measurement, calculation, and the like.

FIG. 3(D) shows the data configuration of specific individual target calculation data 14.

The specific individual target calculation data 14 includes subcutaneous fat percentage, visceral fat percentage, body fat percentage, and weight.

The subcutaneous fat percentage and the visceral fat percentage have the actual measurement values measured with the MRI, DEXA or the like registered in advance. This pre-registration may be made according to an appropriate method such as registering by receiving the values from the server 150 or an external device such as the MRI 10 through the communication unit 111, or registering by manual input of the values by means of the operation unit 114.

The body fat percentage and the weight are variables obtained each time by measurement, calculation, or the like.

The calculation of the body composition of a specific individual and the calculation of the general body composition will be described for the calculation of the body composition.

<Specific Individual Dedicated Calculation Equation>

The body composition of the specific individual can be calculated using the following specific individual dedicated calculation equation. This calculation equation is provided to calculate the fat free mass.

$$f(\rho) = a_2 \cdot 1/\rho + b_2 \cdot W + c_2 \cdot S + d_2 \cdot e_2 \qquad \text{(Equation A)}$$

where, $a_2$ to $e_2$ are predetermined constants, $\rho$ is the resistivity calculated using the actual measurement value of each body site, W is the weight, S is the cross-sectional area of the body site, and L is the site length of the body site. The cross-sectional area S and the site length L can be acquired from the specific individual dedicated variable data 12, the resistivity $\rho$ can be measured from the impedance detected by the impedance detection unit 120, and the weight W can be measured by the load detection unit 133.

The function $f(\rho)$ for obtaining the body composition is a calculation equation in which the polynomial equation of the resistivity $\rho$, the weight W, the cross-sectional area S, and the body site L is fitted to the actual measurement data of the MRI, DEXA, or the like.

The function $f(\rho)$ may be a function of two or more orders.

The body fat percentage can be calculated from the fat free mass and the weight.

The muscle mass, the body fat mass, and the bone mass for every body site can be calculated with the calculation equation similar to the fat free mass.

The body composition of the specific individual can be calculated by an appropriate calculation equation, and the fat free mass can be calculated using the following calculation equation.

$$f(\rho) = a_1 \cdot 1/\rho + b_1 \cdot W + c_1 \qquad \text{(Equation B)}$$

In the equation, $a_1$ to $c_1$ are predetermined constants defined in advance for every body site, $\rho$ is the resistivity calculated using the actual measurement value of each body site, and W is the weight.

The constants $a_1$ to $c_1$ in the calculation equation are corrected for individual use based on the actual measurement data from, for example, the MRI or DEXA to carry out an accurate calculation.

The body composition may be more accurately obtained by using both equation A and equation B after the constants $a_1$ to $c_1$ are corrected.

<General Calculation Equation>

The general body composition can be calculated by the general calculation equation. This general calculation equation may be an equation in which the values defined by height, age, and sex are substituted to the predetermined constants $a_1$ to $c_1$ using equation B.

Figure 4:
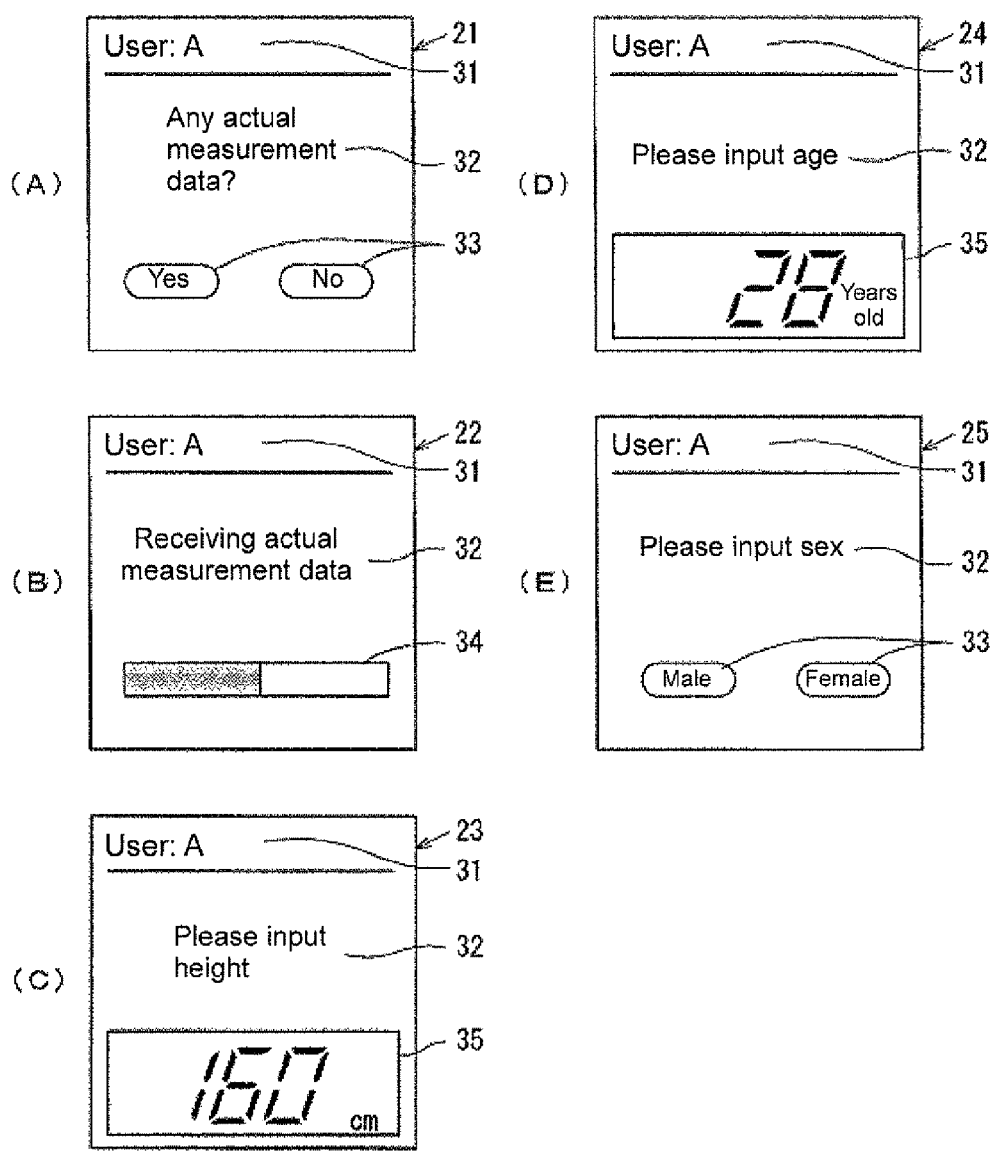
FIG. 4 is an explanatory diagram showing a configuration of a screen displayed on a display unit of the first embodiment.
Figure 5:
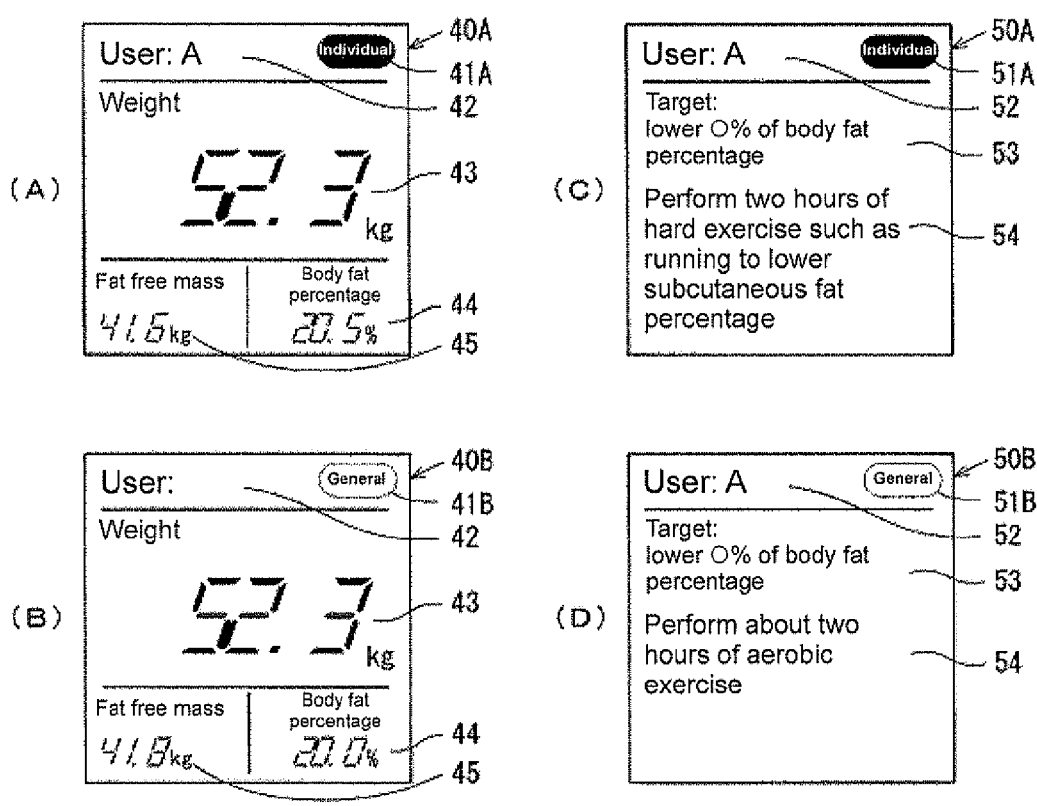
FIG. 5 is an explanatory view showing a configuration of a screen displayed on a display unit of the first embodiment.

FIGS. 4 and 5 are explanatory views showing the configuration of a screen displayed on the display unit 115.

FIG. 4(A) shows a screen configuration diagram of an actual measurement data presence/absence inquiring screen 21 inquiring the presence/absence of the actual measurement data.

The actual measurement data presence/absence inquiring screen 21 includes a user display portion 31, a message display portion 32, and a selection button 33.

The user display portion 31 displays the operating user. The user is displayed by being specified with an appropriate method such as selecting his/her identification information (number, alphabet, etc.) assuming a defined number of users can be registered in advance, or inputting the user name individually.

The message display portion 32 displays a message. In this screen, "any actual measurement data?" is displayed.

The selection button 33 displays options for the user to select operate. In this screen, two options "YES" and "NO" are displayed.

FIG. 4(B) shows a screen configuration diagram of an actual measurement data receiving screen 22 indicating that the actual measurement data is being received.

The actual measurement data receiving screen 22 includes a data receiving amount display portion 34 in addition to the user display portion 31 and the message display portion 32.

The message display portion 32 of the screen displays "receiving actual measurement data".

The data receiving amount display portion 34 is displayed so that the bar extends from the left to the right as the data reception proceeds, and displays the degree of progress of the data reception.

FIG. 4(C) shows a screen configuration diagram of a height input screen 23 for inputting the height.

The height input screen 23 includes a biological basic information input portion 35 in addition to the user display portion 31 and the message display portion 32.

The message display portion 32 of the screen displays "please input height".

The biological basic information input portion 35 displays an input value of the biological basic information (height, age, sex) inputted to the display and operation section 110. In the screen, the height input as the biological basic information is displayed.

FIG. 4(D) shows a screen configuration diagram of an age input screen 24 for inputting the age.

The age input screen 24 includes the user display portion 31, the message display portion 32, and the biological basic information input portion 35.

The message display portion 32 of the screen displays "please input age". The biological basic information input portion 35 of the screen displays the age inputted as the biological basic information.

FIG. 4(E) shows a screen configuration diagram of a sex input screen 25 for inputting the sex.

The sex input screen 25 includes the user display portion 31, the message display portion 32, and the selection button 33.

The message display portion 32 of the screen displays "please input sex".

The selection button 33 of the screen displays two options of "male" and "female".

FIG. 5(A) shows a screen configuration diagram of a specific individual measurement result display screen 40A of the measurement result display screen 40 (40A, 40B) for displaying the measurement result.

The specific individual measurement result display screen 40A includes a calculation type display portion 41 (41A, 41B), a user display portion 42, a weight display portion 43, a fat free mass display portion 44, and a body fat percentage display portion 45.

The calculation type display portion 41 displays a specific individual calculation method adopting mark 41A indicating that it is the measurement result of the specific individual.

The user display portion 42 displays the measured user. The user is the same as the user displayed in the actual measurement data presence/absence inquiring screen 21, and the like.

The weight display portion 43 displays the measured weight.

The fat free mass display portion 44 displays the measured fat free mass. The fat free mass displayed here is the value calculated by the specific individual dedicated calculation equation using the specific individual dedicated variable data 12.

The body fat percentage display portion 45 displays the measured body fat percentage. The body fat percentage displayed here is the value calculated based on the fat free mass and the weight.

FIG. 5(B) shows a screen configuration diagram of a general measurement result display screen 40B of the measurement result display screen 40 (40A, 40B) for displaying the measurement result.

The general measurement result display screen 40B includes a calculation type display portion 41 (41A, 41B), the user display portion 42, the weight display portion 43, the fat free mass display portion 44, and the body fat percentage display portion 45.

The calculation type display portion 41 displays a general calculation method adopting mark 41B indicating that it is the measurement result by a general calculation equation.

The user display portion 42 and the weight display portion 43 are as described above.

The fat free mass display portion 44 displays the value calculated by the general calculation equation using the general calculation variable data 11 for the fat free mass.

The body fat percentage display portion 45 displays the value calculated based on the fat free mass and the weight as a body fat percentage.

FIG. 5(C) shows a screen configuration diagram of a specific individual target display screen 50A of the target display screen 50 (50A, 50B) for displaying the target such as the diet target.

The specific individual target display screen 50A includes a type display portion 51 (51A, 51B), a user display portion 52, a target display portion 53 and a message display portion 54.

The type display portion 51 displays a specific individual calculation method adopting mark 51A indicating that it is the target calculated using the calculation equation of the specific individual.

The user display portion 42 displays the user who calculated the target. The user is the same as the user displayed in the actual measurement data presence/absence inquiring screen 21 and the like.

The target display portion 53 specifically displays the target numerical value. In the illustrated example, how much percentage the body fat percentage is preferably lowered is displayed. The numerical value is calculated dedicated to the specific individual using the specific individual target calculation data 14.

The message display portion 54 displays a message for achieving the target. The message to display here is created based on the value calculated by the specific individual dedicated calculation equation, and more detailed information than when creating with a general calculation equation are displayed. For instance, in the illustrated example, high subcutaneous fat percentage is recognized from the information of the MRI and "perform two hours of hard exercise such as running to lower subcutaneous fat percentage" is displayed.

FIG. 5(D) shows a screen configuration diagram of a general target display screen 50B of the target display screen 50 (50A, 50B) for displaying the target such as the diet target.

The general target display screen 50B includes the type display portion 51 (51A, 51B), the user display portion 52, the target display portion 53 and the message display portion 54.

The type display portion 51 displays a general calculation method adopting mark 51B indicating that it is the target calculated using the general calculation equation.

The user display portion 42 is as described above.

The target display portion 53 specifically displays the target numerical value. In the illustrated example, how much percentage the body fat percentage is preferably lowered is displayed. The numerical value is calculated for general purpose using the general target calculation data 13.

The message display portion 54 displays a message for achieving the target. The message to display here is created based on the value calculated by the general calculation equation. For instance, in the illustrated example, "perform about two hours of aerobic exercise" is displayed.

Figure 6:
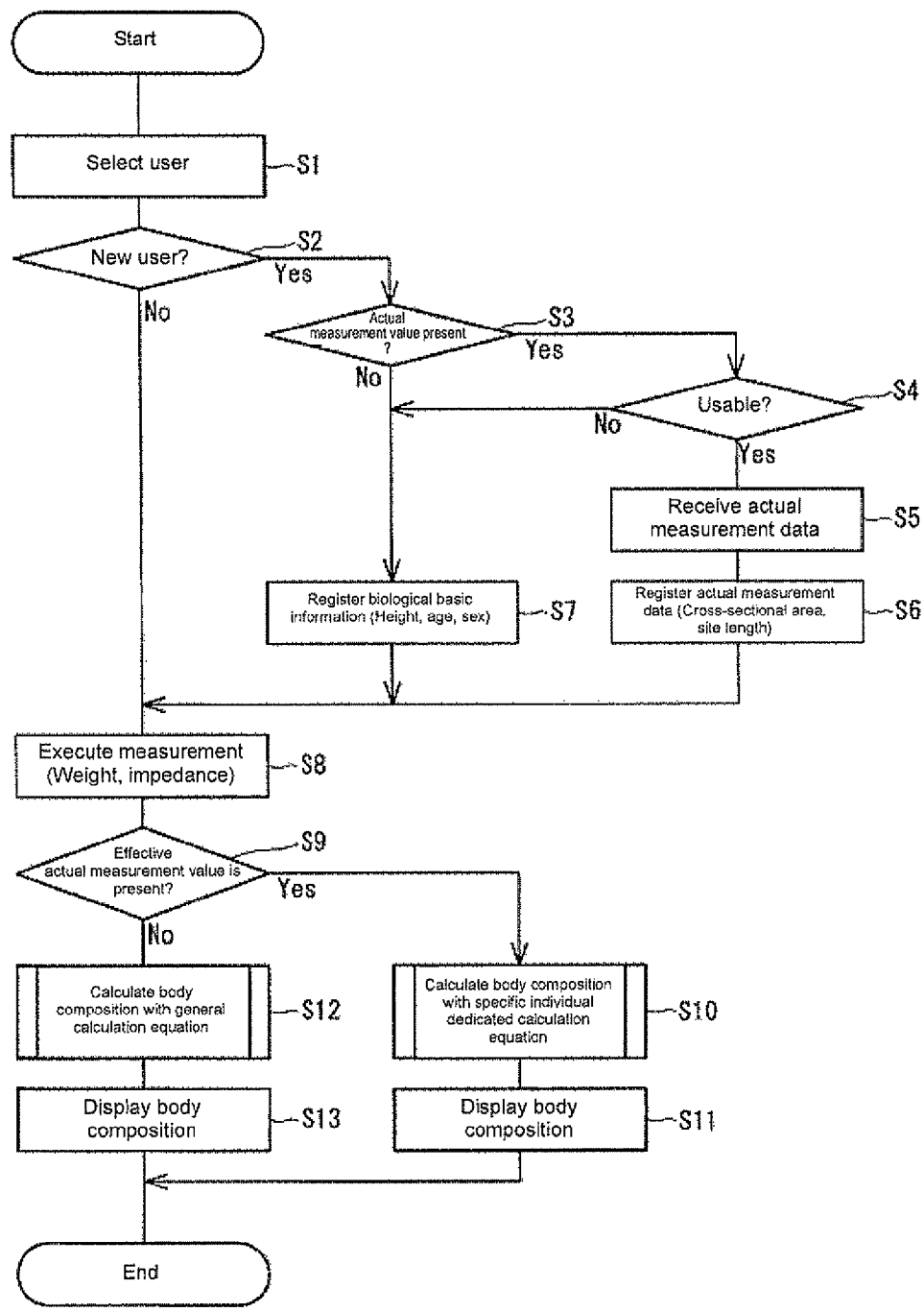
FIG. 6 is a flowchart showing the operation of calculating the body composition of the first embodiment.

FIG. 6 is a flowchart showing the operation in which the control unit 118 of the body composition monitor with scale 100 calculates the body composition. This operation may be started at an appropriate timing such as starting with the detection that the user got on the upper surface cover unit 135 by the load detection unit 133 as the trigger or starting by the operation of the operation unit 114 by the user.

The control unit 118 executes user selection (step S1). In this user selection, a user selection screen (not shown) is displayed on the display unit 115, and the user number is selected by the operation unit 114. This user selection method is not the sole case, and the user may be specified by an appropriate method such as manually inputting the user name or selecting the manually inputted and registered user name.

If a new user (step S2: Yes), the control unit 118 displays the actual measurement data presence/absence inquiring screen 21, and checks the presence/absence of the actual measurement value (step S3). If "Yes" of the selection button 33 is selected, determination is made that the actual measurement value is present (step S3: Yes), and the control unit 118 displays the actual measurement data receiving screen 22 and receives the actual measurement data (step S4). The reception of the actual measurement data may be from the external device such as the server 150 or the MRI 10 through the communication unit 111.

The control unit 118 then determines whether or not the received actual measurement data is usable (step S5). Whether or not usable may be determined from whether or not the measurement date of the received actual measurement data is within a predetermined period from the current date and time.

If usable (step S5: Yes), the control unit 118 registers the actual measurement data in the specific individual dedicated variable data 12 and the specific individual target calculation data 14 (step S6). The actual measurement data to register here is the actual measurement value measured with a device such as the MRI, the DEXA such as the cross-sectional area, the site length, the subcutaneous fat percentage, and the visceral fat percentage.

If the actual measurement value is absent (step S3: No), or if the actual measurement value is not usable (step S5: No), the control unit 118 sequentially displays the biological basic information input screen (23, 24, 25) to request the user to register the biological basic information by manual input (step S7). The biological basic information such as the height, the age, and the sex of the user are then inputted with the operation unit 114, and the control unit 118 registers such information in the general calculation variable data 11.

If the registration of the actual measurement data is completed (step S6), the registration of the biological basic information is completed (step S7) or it is not a new user (step S2: No), the control unit 118 executes the measurement of the weight and the impedance (step S8). This measurement is carried out with the user correctly standing on the upper surface cover unit 135.

The control unit 118 determines whether or not the effective actual measurement data is registered in the specific individual dedicated variable data 12 (step S9). This determination is made from the date and time at which the cross-sectional area and the site length are registered in the specific individual dedicated variable data 12, the current date and time, and the change in body composition. For instance, if the registered date and time is closer than a predetermined period, determination is made as the effective actual measurement data. Although the registered date and time is before the predetermined period, determination is made as the effective actual measurement data if the change in the body composition being continuously measured is smaller than or equal to a predetermined amount since there is no particular change.

If determined as effective (step S9: Yes), the control unit 118 calculates the body composition using a specific individual dedicated calculation equation A (step S10), displays the calculated body composition on the specific individual measurement result display screen 40A (step S11), and terminates the process. The specific individual calculation method adopting mark 51A indicating that the calculation equation of the specific individual is used is also displayed in the specific individual measurement result display screen 40A.

If determined as not effective (step S9: No), the control unit 118 calculates the body composition using a general calculation equation B (step S12), displays the calculated body composition on the general target display screen 50B (step S13), and terminates the process. The general calculation method adopting mark 51B indicating that the general calculation equation is used is also displayed in the general target display screen 50B.

Figure 7:
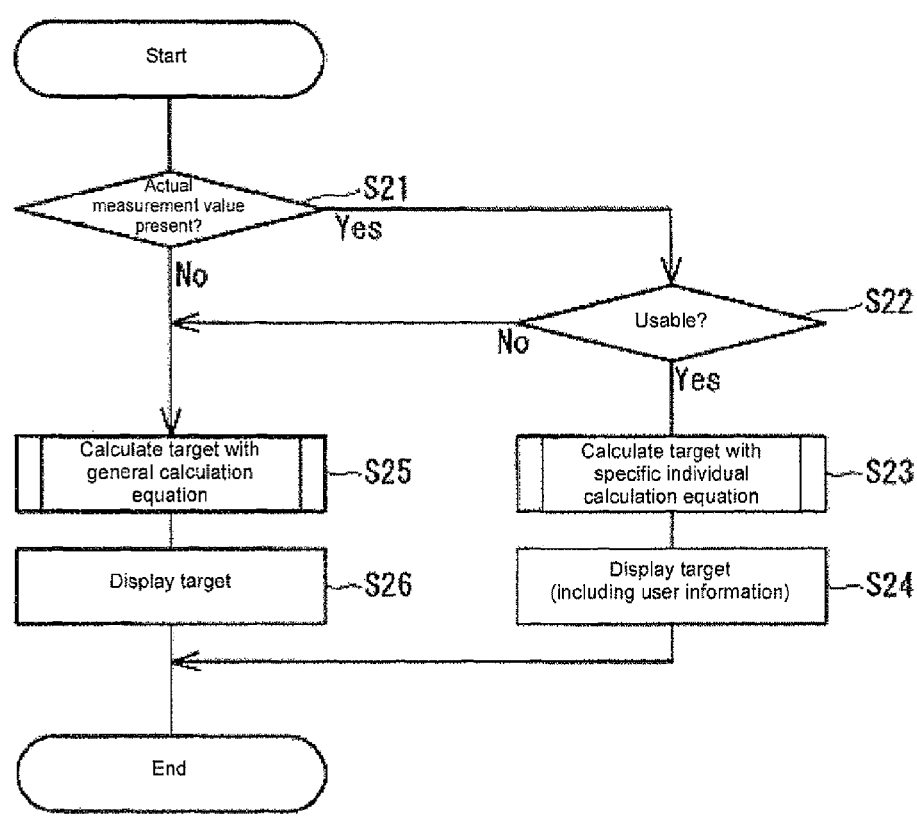
FIG. 7 is a flowchart showing the operation of obtaining the target of the first embodiment.

FIG. 7 is a flowchart showing the operation in which the control unit 118 of the body composition monitor with scale 100 obtains the target.

The control unit 118 determines whether or not the actual measurement value of the operating user (or measuring user) is present from whether or not the specific individual target calculation data 14 is registered (step S21).

If registered (step S21: Yes), the control unit 118 determines whether or not usable (step S22). Whether or not usable may be determined from whether or not the measurement date of the registered actual measurement data is within a predetermined period from the current date and time.

If usable (step S22: Yes), the control unit 118 calculates the target using the specific individual calculation equation (step S23). The specific individual calculation equation for calculating the target may be an appropriate calculation equation for calculating the target value using the subcutaneous fat percentage and the visceral fat percentage registered in advance as variables defined in the specific individual target calculation data 14 and the measured body fat percentage and weight.

The control unit 118 displays the calculated target on the specific individual target display screen 50A (step S23), and terminates the process.

If the actual measurement data is not usable (step S22: No), or the actual measurement data is not registered (step S21: No), the control unit 118 calculates the target using the general calculation equation (step S25). The general calculation equation for calculating the target may be an appropriate calculation equation for calculating the target value using the body fat percentage and the weight measured as variables defined in the general target calculation data 13.

The control unit 118 displays the calculated target on the general target display screen 50B (step S26), and terminates the process.

According to the above configurations and operations, the body composition can be accurately calculated using the data acquired by another device (MRI 10 etc.), and the satisfaction level of the user can be enhanced.

Upon obtaining the body composition such as the fat free mass, the calculation is carried out with the specific individual dedicated calculation equation A using the actual measurement data calculated in the MRI 10 or the like, so that the body composition can be calculated at higher accuracy than the estimating calculation using the general calculation equation B.

Since the specific individual calculation method adopting mark 41A or the general calculation method adopting mark 41B is displayed in the measurement result display screen 40, the user can visually check whether the current measurement result is from the estimation or is of high accuracy using the actual measurement data in another device.

Furthermore, since the presence and absence of the actual measurement data is inquired by the actual measurement data presence/absence inquiring screen 21, the actual measurement data can be registered if the actual measurement data is present to accurately calculate the body composition, and the body composition can be calculated with the general estimating calculation if the actual measurement data is absent. Therefore, the user can appropriate select the accurate calculation and the estimating calculation.

Whether or not the registered actual measurement data is usable is determined, and the calculation is carried out using the actual measurement data only when the actual measurement data is usable, and hence the calculation result can be prevented from becoming a poor accuracy although the actual measurement data is used. Thus, the calculation can be automatically carried out with the best method of the calculation using the actual measurement data and the estimating calculation, and the error of the data of the measurement result can be prevented from becoming large while displaying the specific individual calculation method adopting mark 41A.

If the actual measurement data is present, the actual measurement data measured with another device such as the MRI 10 can be received and a highly accurate calculation can be executed, so that the user can accurately measure the body composition without manually registering the biological basic information such as height, age, and sex. Therefore, the user with the actual measurement data can obtain the accurate measurement result by simply getting on the upper surface cover unit 135 of the body composition monitor with scale 100, making a user select, and selecting actual measurement data present. In other words, the troublesome manual input task can be eliminated, and high convenience can be realized.

If the actual measurement data is present, the calculation of the target also can be carried out with high accuracy. In other words, whether or not the diet is easy differs among individuals depending on the state of the body composition such as great amount of subcutaneous fat or great amount of visceral fat. The state of the body composition in which there is difference among individuals can be grasped by using the actual measurement data of the other device such as the MRI 10, and the appropriate target setting corresponding to the state of the body composition of the user can be carried out to notify the user.

A configuration of determining whether or not usable when using the actual measurement data is adopted, but the degree of reflection can be differed by the oldness of the actual measurement data when determined as usable. In this case, the correction ratio of the constants $a_1$ to $c_1$ for correcting using mainly equation B is made smaller as the actual measurement data becomes older, and a general constant defined with the biological basic information may be set if older than a predetermined range or more. Thus, the general calculation equation is approached little by little as the actual measurement data by the other device becomes older to smoothly transition to the general calculation equation.

In this case, the user may be notified that the actual measurement data is getting older by displaying the correction ratio on the screen. The user then can again measure with the MRI 10 or the like and update the actual measurement data.

Second Embodiment

In a second embodiment, a description will be given of a body composition monitor with scale for optimizing the estimation equation of the body composition, the body composition value, the determination of the diet tendency, and the like according to the individual using data measured by devices such as an MRI (Magnetic Resonance Imaging), CT (Computed Tomography) or DEXA (Dual Energy X-Ray Absorptiometry) installed in medical facilities or the like.

In the second embodiment, the body composition monitor with scale 100, the server 150, and the biological information acquiring system 101 that are the same as the first embodiment are used.

The storage unit 112 stores detailed measurement data instead of the information described in the first embodiment. The detailed measurement data may include highly accurate information about the body composition measured in a device different from the body composition monitor with scale 100 such as the body fat percentage or visceral fat mass measured by CT, MRI, DEXA or the like.

The body composition measurement program is stored for the program stored in the ROM or the like of the control unit 118.

Other configurations are the same as those in the first embodiment, and thus the detailed description will be omitted.

Figure 8:
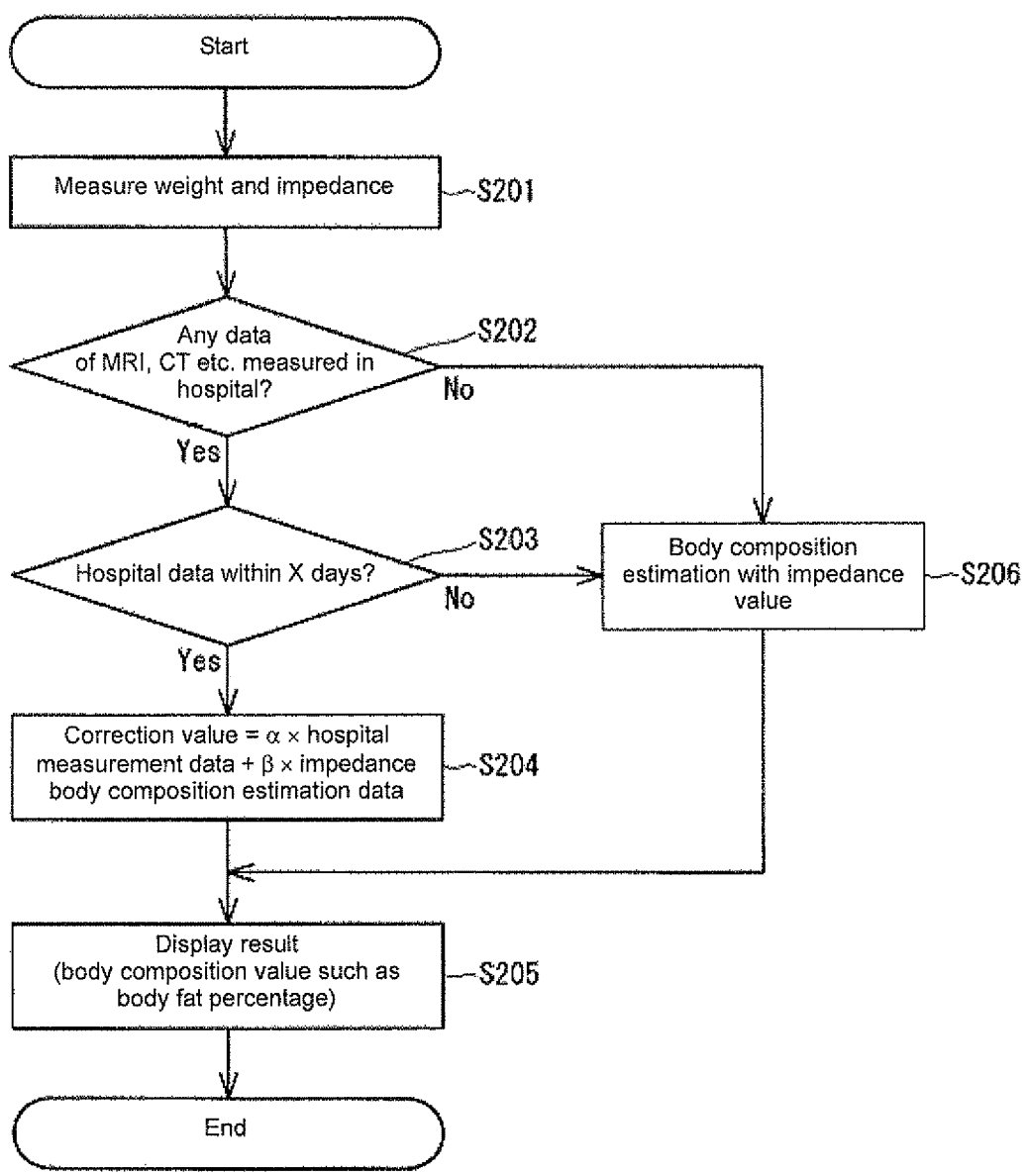
FIG. 8 is a flowchart showing operation of body composition measurement process of a second embodiment.

FIG. 8 is a flowchart showing the operation of the body composition measurement process executed by the control unit 118 according to the body composition measurement program.

The control unit 118 measures the weight of the user by the load detection unit 133 and also measures the impedance of the user by the impedance detection unit 120 (step S201).

The control unit 118 accesses the server 150, and checks whether or not there is detailed measurement data by MRI, CT, DEXA, or the like in hospitals and the like (step S202). In this case, the detailed measurement data is acquired if present, and stored in the storage unit 112.

If the detailed measurement data is present (step S202: Yes), the control unit 118 determines whether or not the measurement date of the relevant detailed measurement data is within a predetermined number of days from the present (step S203).

If within a predetermined number of days (step S203: Yes), the control unit 118 uses the acquired detailed measurement data to correct the calculation (estimation) of the body composition based on the impedance measured in step S201, and calculates the corrected body composition value (step S204).

The body composition value obtained here may be the body fat percentage, the visceral fat level, the muscle percentage, the basal metabolism, or pluralities of the same, and can be calculated according to a known calculation method. The body composition value after the correction in this case can be obtained with the following equation.

Corrected body composition value=α×detailed measurement data+β×impedance body composition estimation data  (Equation 2)

*α, β: weight coefficients where, α is preferably a coefficient that becomes greater as the measurement date of the detailed measurement data becomes closer to the present date.

Not limited to using equation 2 above, the calculation may be carried out using equation A and equation B described in the first embodiment.

If the detailed measurement data does not exist (step S202: No), or if the detailed measurement data is in the past by a predetermined number of days or more from the present (step S203: No), the control unit 118 calculates (estimates) the body composition by the impedance value acquired in step S201 (step S206).

The control unit 118 displays the results measured in step S204 or step S206 on the display unit 115 (step S205), and terminates the process.

Therefore, if the most recent detailed measurement data is present, a highly accurate body composition value corrected using such detailed measurement data can be calculated and displayed, and the body composition value calculated without correcting can be displayed if the most recent detailed measurement data is not present.

Figure 9:
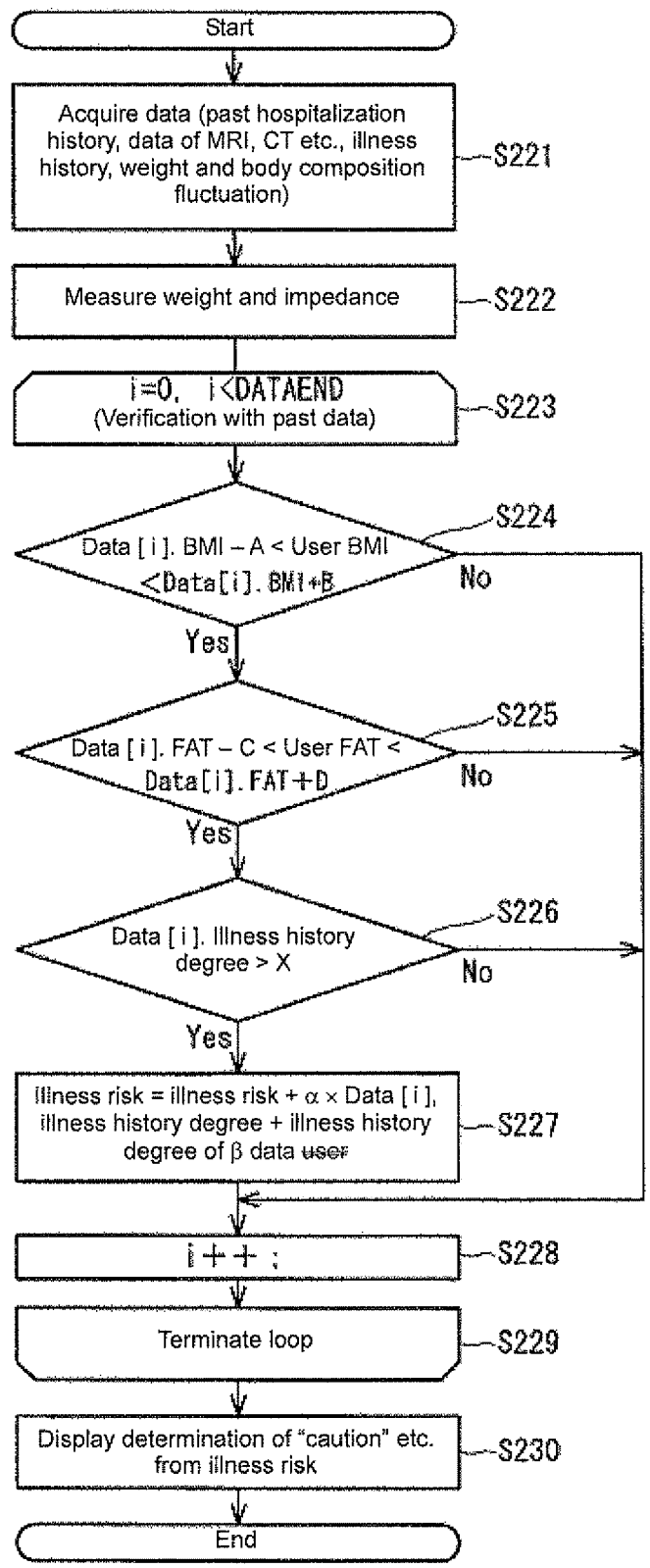
FIG. 9 is a flowchart of the operation in which the health support for diet is carried out in the second embodiment.

FIG. 9 is a flowchart of the operation in which the control unit 152 of the server 150 carries out a health support for diet adapted to each individual. The health support for diet displays caution etc. if there is an illness risk due to impossible diet or the like.

The control unit 152 acquires the past data stored in the storage unit 155 (step S221). The past data is based on the past hospitalization history, the data of the MRI and the CT, the illness itinerancy, the weight, the body composition fluctuation, or the like, and includes the BMI (Body Mass Index), the FAT (body fat percentage data), the in FAT (visceral fat data), the skeletal muscle percentage, or the like. The data to acquire here is preferably of another user having, the same body build, age, illness history, and the like as the user. The data of a great number of people whose conditions are close to the user then can be collected and used for determination.

The control unit 152 acquires the measurement results of the weight and the impedance from the body composition monitor with scale 100 (step S222).

The control unit 152 substitutes the value "0" to the variable i and starts the verification of repeating from the beginning to the end (DATAEND) of the data acquired in step S221 (step S223).

The control unit 152 then determines whether or not the BMI value (user BMI) of the user is within a predetermined range (range from −A to B) having the BMI (indicated as Data[i].BMI) of the ith data (data of another person) as the center (step S224). This determination can be executed with the following equation.

$$\text{Data}[i].\text{BMI} - A < \text{user BMI} < \text{Data}[i].\text{BMI} + B \quad \text{(Equation 3)}$$

*Data[i]. BMI: BMI of ith data,
A, B: coefficients

In this case, determination can be made that the user BMI is within a predetermined range if between −A and +B of Data[i]. BMI.

The control unit 152 then determines whether or not the FAT value (user FAT) of the user is within a predetermined range (range from −C to D) having the FAT (indicated as Data[i]. FAT) of the ith data (data of another person) as the center (step S225). This determination can be executed with the following equation.

$$\text{Data}[i].\text{FAT} - C < \text{user FAT} < \text{Data}[i].\text{FAT} + D \quad \text{(Equation 4)}$$

*Data[i]. FAT: FAT of ith data,
C, D: coefficients

In this case, determination can be made that the user FAT is within a predetermined range if between −C and +D of Data [i]. FAT.

The control unit 152 then determines whether or not the illness history degree of the user or the illness history degree (Data[i]. illness history degree) of the ith data (data of another person) is greater than or equal to a predetermined threshold value (X) (step S226). The more severe the illness or the greater the number of times, the illness history degree is set so as to take a higher value. The determination can be executed with the following equation.

$$\text{Data}[i].\text{illness history degree} > X \quad \text{(Equation 5)}$$

*Data[i]. illness history degree: ith illness history,
X: threshold value

If determined as YES in all the steps S224 to S136, the control unit 152 calculates the illness risk with the following equation.

$$\text{Illness risk} = \text{illness risk} + \alpha \times \text{Data}[i].\text{illness history degree} + \text{illness history degree of } \beta \text{ data} \quad \text{(Equation 6)}$$

If determined as outside the predetermined range in one of steps S224 to S226 (step S224: No, S225: No, S226: No), the control unit advances the process to the next step without determining the illness risk.

The control unit 152 adds 1 to the variable i and returns the process to step S224 (step S228), and repeatedly executes the processes of steps S224 to S227 (step S229).

The control unit 152 checks the illness risk, displays a display such as "caution" as necessary on the display unit 115 of the body composition monitor with scale 100 (step S230), and terminates the process.

According to such operation, the user can know about the illness risk if it exists. If there are greater number of people with high illness history degree among the people with a body composition value similar to the user, the illness risk becomes higher by that much, and thus the user is able to know whether or not there are many people with illness history in the people with body composition value similar to himself/herself and can pay attention to the illness.

In the present example, the determination is made on the BMI and the FAT, but this is not the sole case, and the determination on the visceral fat and the determination on the skeletal muscle percentage maybe additionally made. In this manner, the illness risk can be determined compared to the people with similar body composition.

Figure 10:
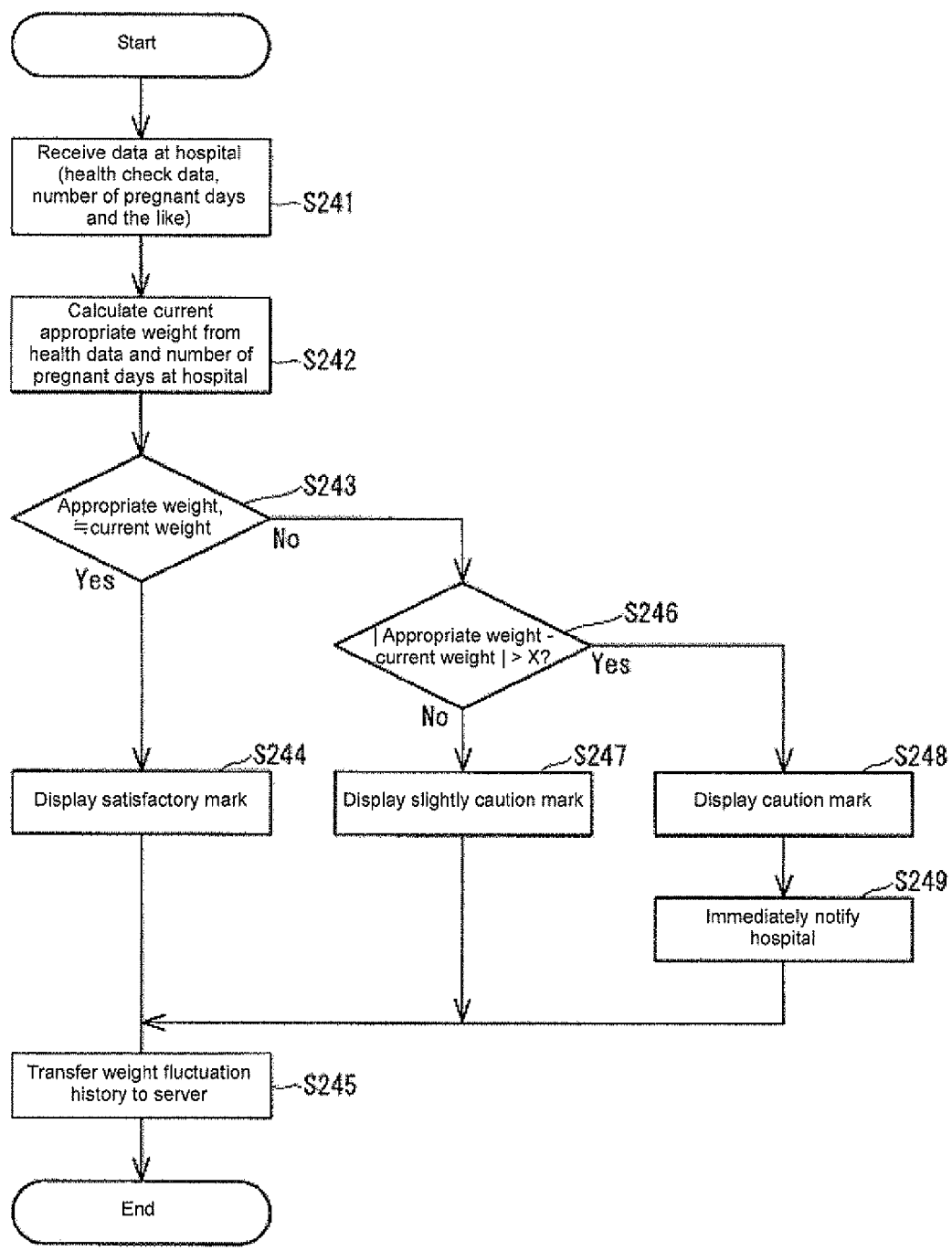
FIG. 10 is a flowchart of the operation in which the health support of a pregnant woman is carried out in the second embodiment.

FIG. 10 is a flowchart of the operation for the control unit 118 of the body composition monitor with scale 100 to perform the health support of a pregnant woman.

The control unit 118 first receives the health check data, the number of pregnant days, and the like measured in hospitals and the like from the server 150 (step S241).

The control unit 118 calculates the current appropriate weight from the acquired health check data and the number of pregnant days (step S242). The appropriate weight may be calculated in the server 150 and transmitted to the body composition monitor with scale 100.

The control unit 118 performs weight measurement by the load detection unit 133, and determines whether or not the measured current weight is close to the appropriate weight (step S243). This determination may be made depending on whether or not a difference value of the appropriate weight and the current weight is within a predetermined value.

If the current weight is close to the appropriate weight (step S243: Yes), the control unit 118 displays a satisfactory mark on the display unit 115 (step S244), and advances the process to step S245.

If the current weight is not close to the appropriate weight (step S243: No), the control unit 118 determines whether or not the appropriate weight and the current weight is greater than a predetermined threshold value X (step S246). The threshold value X is a threshold value at which the mother and the fetus are considered dangerous, and can be appropriately set such as set by the user with the advice from the doctor or set by the attending doctor while being periodically changed according to the state of the mother.

If smaller than or equal to the threshold value X (step S246: No), the control unit 118 displays a slightly caution mark on the display unit 115 (step S247) and advances the process to step S245.

If greater than the threshold value X (step S246: Yes), the control unit 118 displays a caution mark on the display unit 115 (step S248), immediately notifies the hospital (step S249), and advances the process to step S245. The notification to the hospital is executed by transmitting data of the user information and the caution information to the terminal or the e-mail address of the hospital set in advance.

The control unit 118 transmits the measurement weight to the server 150 and causes the server to store the same as the weight fluctuation history (step S245). The doctors, nurses, and the like at the hospital then can access the server 150 from an appropriate terminal and check at any time whether the progress is satisfactory or not.

As described above, in the body composition monitor (body composition monitor with scale 100) including the impedance measurement means (impedance detection unit 120) for the biological information acquiring means, the biological component information (associated biological information) includes associated body composition information (body fat percentage and visceral fat measured with MRI, CT, DEXA or the like) indicating the body composition of the living body measured with a method different from the impedance measurement, the correction means (control unit 118 that executes step S204) is configured to carry out correction based on the associated body composition information when obtaining the body composition of the living body from the impedance, and the output means (display unit 115) is configured to output the corrected body composition information (body fat percentage, visceral fat level, muscle percentage, basal metabolism, or pluralities of the above) as corrected information.

Therefore, the body composition estimation algorithm can be optimized according to each individual by looking at the correlation between the body fat percentage and the visceral fat measured by the MRI, the CT, the DEXA or the like at the hospital and the impedance value measured with the body composition monitor. The error that occurs as the electrical characteristics more or less differ depending on the person can be made small in the body composition estimation using the impedance value.

In particular, the body composition can be more accurately estimated using the impedance value in even children and athletes in which the estimation error of the body composition tends to become large.

Furthermore, the user can be notified that the degree of danger of the illness is high when the illness history is great in people whose value of body composition is close to that of the user according to the health support for diet. The user is then able to know that his/her body composition is in a state of easily becoming ill, which becomes a momentum to improve the constitution. The improvement of the value of the body composition from the state of easily becoming ill can be known even while improving the constitution.

In particular, the possibility of a disease can be known by accessing the server 150 even with the body composition monitor with scale 100 installed at home, so that the constitution check can be carried out at home.

The weight fluctuation of the pregnant woman that is the user may be checked and notification may be made to the user and the hospital when there is danger to the mother and the fetus according to the health support of the pregnant woman. Therefore, the user can find pregnancy toxicosis at an early stage thus enhancing the safety of delivery.

In particular, the possibility of pregnancy toxicosis can be known by accessing the server 150 even with the body composition monitor with scale 100 installed at home, so that the safety of delivery can be checked at home.

Third Embodiment

The body composition monitor with scale, which is one type of biological information acquiring device, will be described in the third embodiment for measuring the contact impedance of the skin by a device installed at medical facilities and the like, and correcting the body composition to be measured with the body composition monitor by such contact impedance of the skin.

A method of measuring the impedance of the user and measuring (estimating) the body composition such as visceral fat and subcutaneous fat is conventionally known. However, a very small error may occur as the contact impedance of the skin differs depending on the dry state of the skin of the user.

The body composition monitor with scale of the third embodiment, on the other hand, aims to enhance the measurement accuracy by making the correction according to the contact impedance of the skin serving as the actual measurement data measured with another device. This will be specifically described below in conjunction with the drawings.

In the third embodiment, the weigh and body composition monitor 100, the server 150, and the biological information acquiring system 101 same as the first embodiment are used.

In addition to the user information described in the first embodiment, the storage unit 112 stores the contact impedance of the skin measured with a separate device.

Other configurations are the same as the first embodiment, and hence the detailed description thereof will be omitted.

Figure 11:
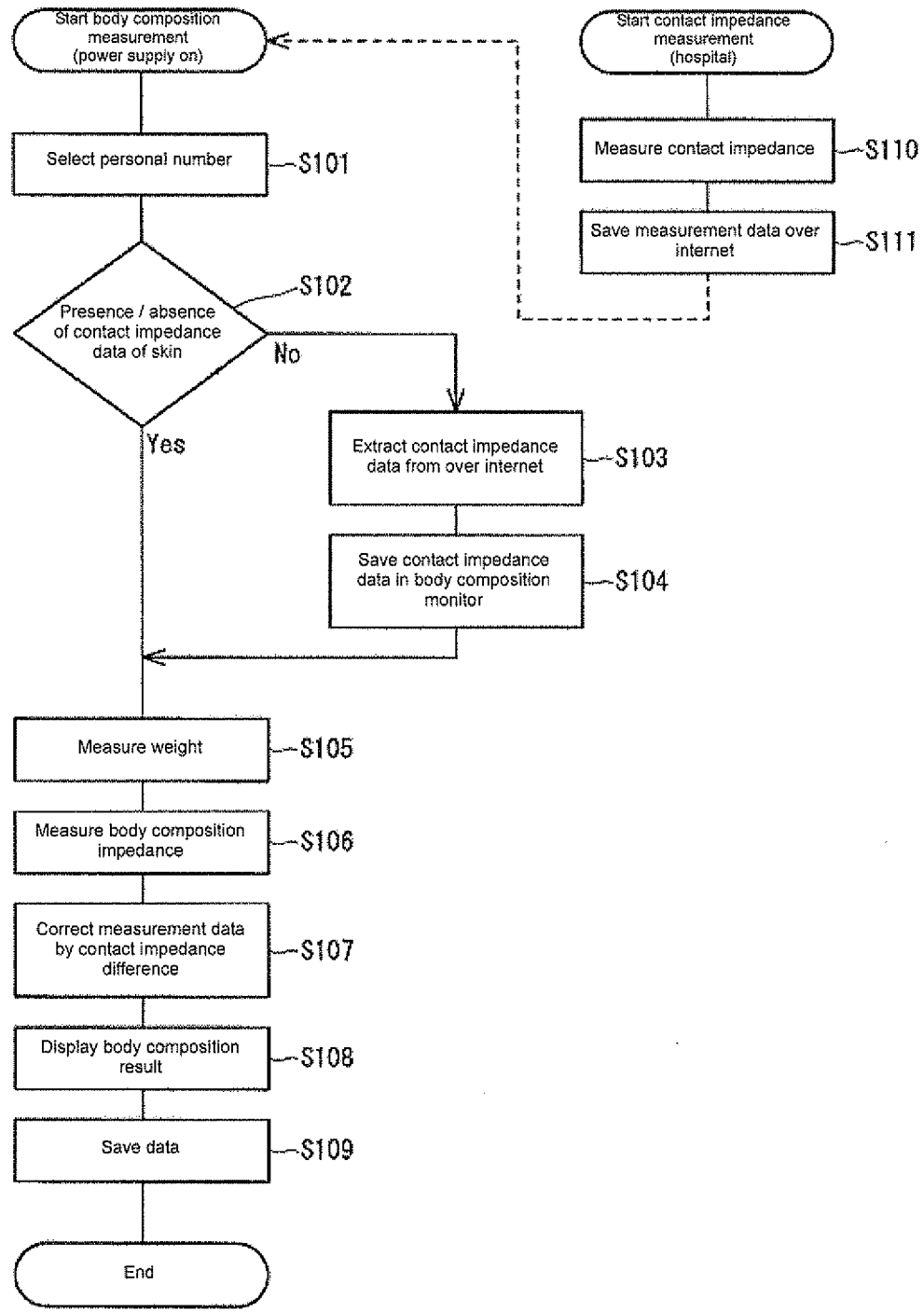
FIG. 11 is a flowchart showing the operation of a body composition monitor with scale according to a third embodiment.

FIG. 11 is a flowchart showing the operation executed by the control unit 118 of the body composition monitor with scale 100 according to the body composition measurement program.

Prior to using the body composition monitor with scale 100, the user measures the contact impedance data of the skin with a contact impedance measurement device separately arranged in facilities such as the hospital. In other words, the contact impedance measurement device arranged in hospitals and the like measures the contact impedance of the user (step S110), and registers the measurement data in the server 150 (step S111). In this case, the user information specifying the user are also preferably acquired and registered in the server 150. Thus, the user carries out the measurement of the body composition by the body composition monitor with scale 100 after measuring the contact impedance of the skin.

The control unit 118 of the body composition monitor with scale 100 allows the user to select a personal number with the operation unit 114 (step S101).

The control unit 118 accesses the storage unit 112 to check the presence or absence of the contact impedance data of the skin (step S102).

If the contact impedance of the skin is absent (step S102: No), the control unit 118 extracts the contact impedance data from the server 150 (step S103) and stores such contact impedance data in the storage unit 112.

If the contact impedance of the skin is present (step S102: Yes), the control unit 118 executes the weight measurement by the weight measurement section 130 (step S105), and executes the body composition impedance measurement by the impedance detection unit 120 (step S106).

The control unit 118 corrects the measurement data of the body composition impedance by the contact impedance of the skin (step S107). The correction in this case is executed by the following equation 1. The body composition impedance true value is thereby obtained, and the body composition of the subcutaneous fat, the visceral fat, and the like can be accurately estimated.

Body composition impedance value−contact impedance value=body composition impedance true value (impedance correction value) (Equation 1)

The control unit 118 displays the measurement result of the body composition after the correction on the display unit 115 (step S108) and stores the data in the storage unit 112 (step S109).

As described above, the body composition monitor (body composition monitor with scale 100) including the impedance measurement means (impedance detection unit 120) for the biological information acquiring means has a configuration in which the biological component information (associated biological information) includes the contact impedance of the skin and the correction means (control unit 118 that executes step S107) corrects the body composition information of the living body based on the contact impedance of the skin.

Therefore, the body composition measured by the body composition monitor with scale 100 can be corrected using the contact impedance of the skin measured in hospitals and the like. Therefore, the accuracy of the body composition measured by the body composition monitor with scale 100 can be enhanced.

In other words, the measurement result has error due to difference in the contact impedance of the skin in the method of measuring the body composition by the impedance using the electrode units 121, 136 even if the body composition is exactly the same. This error is corrected using the contact impedance of the skin to measure a more accurate body composition.

Furthermore, the contact impedance of the skin is separately measured in hospitals and the like, so that an accurate measurement result of the body composition can be easily obtained in the body composition monitor with scale 100 in the subsequent measurement of the daily body composition.

The contact impedance of the skin may be stored in the storage unit 112 of the body composition monitor with scale 100, and hence can be used once stored without accessing the server 150. Therefore, the handling of the body composition monitor with scale 100 is facilitated.

In the example described above, the body composition measuring section of the body composition monitor with scale 100 has been described as both hands—both feet type, but is not limited thereto and the both hand type or the both feet type body composition monitor may be used. In this case as well, the body composition can be accurately measured by performing correction with the contact impedance.

Fourth Embodiment

As a fourth embodiment, an electronic thermometer for correcting the parameters in the body temperature calculation algorithm with the subcutaneous fat measurement data by the body composition monitor will be described.

A method of placing the mercury type thermometer at the armpit until the surface temperature and the deep temperature become equilibrium is conventionally provided as a method of measuring the deep temperature of the living body. As this method takes time, a method of predicting the equilibrium point by fitting the mode of temperature change until the surface temperature and the deep temperature become equilibrium to the equation, and predicting the equilibrium point as the body temperature is currently proposed. However, the mode of temperature change differs depending on the body composition or the like of the living body, and thus has drawbacks in that the accuracy differs depending on the living body and in that a time of a certain extent is required until the estimation.

The electronic thermometer of the fourth embodiment, on the other hand, aims to accurately measure the deep temperature in a short time by using the data of the separately measured body composition. This will be specifically described below in conjunction with the drawings.

Figure 13:
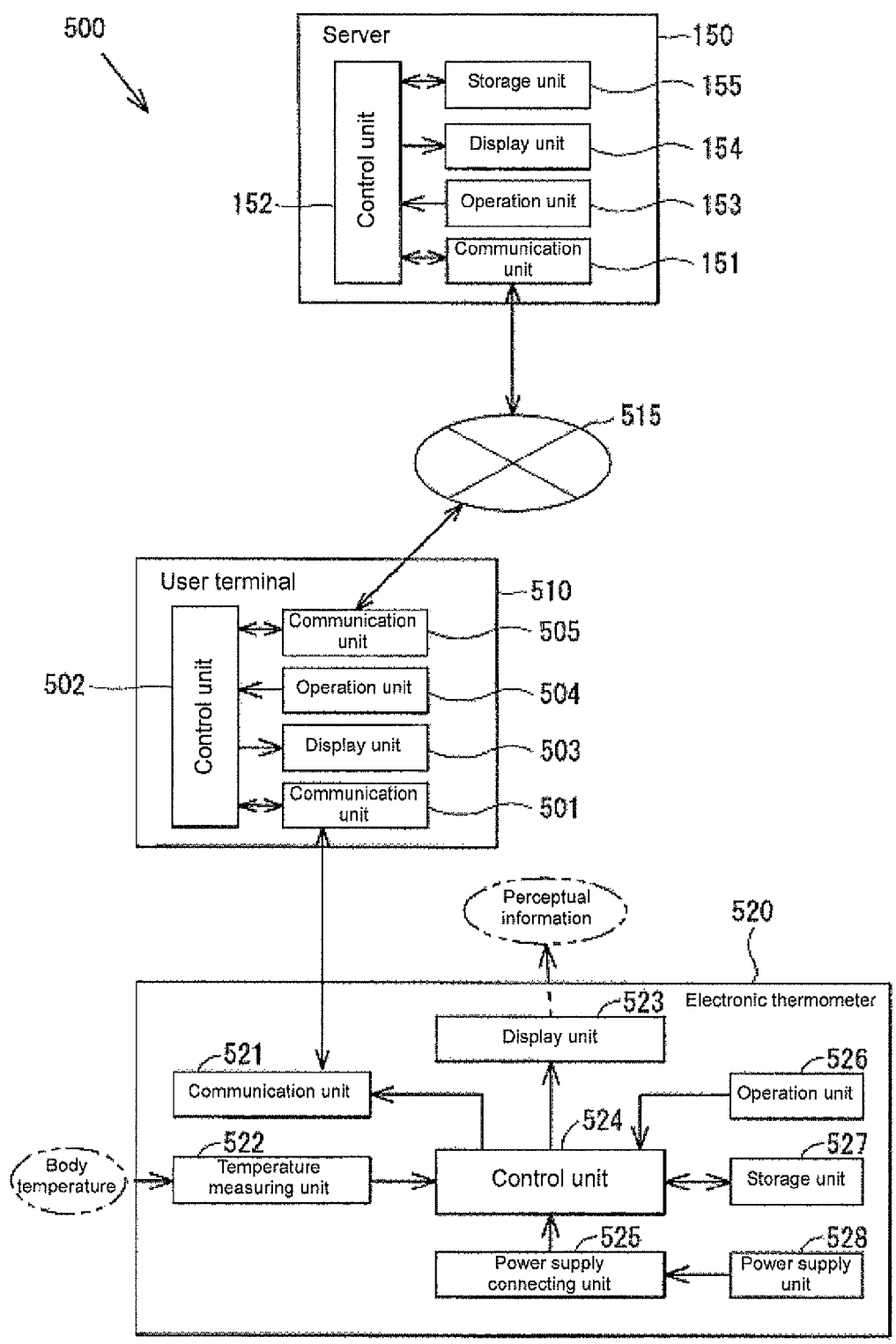
FIG. 13 is a block diagram showing a system configuration of a biological information acquiring system of the fourth embodiment.

FIG. 12(A) is a perspective view showing an outer appearance of an electronic thermometer 520, FIG. 12(B) is an explanatory view showing a heat conduction model of the electronic thermometer 520, and FIG. 13 is a block diagram showing a system configuration of the biological information acquiring system 500.

As shown in FIG. 12(A), the electronic thermometer 520 includes a display unit 523 and an operation unit 526 at the main body portion, and a temperature measuring unit 522 at the distal end. The electronic thermometer 520 measures the body temperature of the user by placing the temperature measuring unit 522 under the arm or under the tongue.

As shown in FIG. 13, the biological information acquiring system 500 includes the server 150 and the user terminal 510 connected to the Internet 515 by wire or wirelessly, and the electronic thermometer 520 connected to the user terminal 510 by wire or wirelessly.

The server 150 has been described in the first embodiment, and thus the same reference numerals are denoted on the same elements and the detailed description thereof will be omitted. The server 150 executes an appropriate process such as a process of receiving data from the electronic thermometer 520 through the user terminal 510, and storing the data in the storage unit 155, a calculation process based on such data and the data stored in the storage unit 155, and a process of transmitting parameters or the like to the electronic thermometer 520.

The server 150 is also connected to the body composition monitor with scale 100 described in the first and second embodiments through the Internet 515, and stores the body composition data received from the body composition monitor with scale 100 in the storage unit 155 along with the user information. The server 150 also performs the process of acquiring the necessary data such as the subcutaneous fat thickness from the stored body composition data, and transmitting the same to the electronic thermometer 520.

The user terminal 510 is configured by a personal computer, or the like, and includes a communication unit 501, a control unit 502, a display unit 503, an operation unit 504, and a communication unit 505. The communication unit 501 may include an appropriate communication interface such as USB (Universal Serial Bus) for wire connecting or the Bluetooth (registered trademark) for wireless communication. The communication unit 505 can include an appropriate communication device such as wire connecting LAN board or wirelessly communicating wireless LAN board.

The user terminal 510 has a function of acquiring the data from the electronic thermometer 520 through the communication unit 501 and transmitting the data to the server 150, and a function of transmitting the data received from the server 150 to the electronic thermometer 520.

The user terminal 510 is not limited to the personal computer, and may be an appropriate device such as a portable information processing device including PDA (Personal Digital Assistants) and portable telephone.

The electronic thermometer 520 includes a communication unit 521, a temperature measuring unit 522, a display unit 523, a control unit 524, a power supply connecting unit 525, a storage unit 527, and a power supply unit 528.

The communication unit 521 may include an appropriate communication interface such as USB (Universal Serial Bus) for wire connecting or the Bluetooth (registered trademark) for wireless communication.

The temperature measuring unit 522 is configured by a probe (not shown) at the distal end and a temperature sensor (not shown) to measure temperature. The temperature measuring unit 522 transmits the measured temperature to the control unit 524 as a detection signal.

The display unit 523 includes a display device such as liquid crystal, and displays information according to a display control signal from the control unit 524. The information to display may be information about the measurement body temperature such as deep body temperature.

The control unit 524 is driven by power received from the power supply unit 528 through the power supply connecting unit 525, and executes reception (detection) of the detection signal from the temperature measuring unit 522, and power supply (power supply) and operation control (display control) on the communication unit 521, the display unit 523, and the storage unit 527. The control unit 524 also executes a process of correcting the measurement temperature and calculating the deep temperature with reference to the detection signal received from the temperature measuring unit 522 and the parameters stored in the storage unit 527.

The storage unit 527 stores a program for accessing the server 150 through the user terminal 510 and acquiring necessary data such as subcutaneous fat thickness, a body temperature measurement program for correcting the measured temperature with parameters and calculating a deep temperature, parameters, and the like. The probe heat capacity of the temperature measuring unit 522 and the subcutaneous fat thickness of the user received through the user terminal 510 are also stored.

The way of thinking the heat conduction model used in the fourth embodiment will now be described.

First, if the electronic thermometer 520 is fixed at the measurement site (under the arm etc.) of the human body, the detected temperature T(t) can be simply expressed as a function of time, as shown in equation 7.

$$T(t) = (T_0 - T_1)\exp^{(-t/\tau)} \quad \text{(Equation 7)}$$

$T_0$: heat source temperature, $T_1$: probe initial temperature, $\tau$: probe heat capacity/heat time constant of measurement site Equation 8 below is obtained by solving equation 7 for $T_0$.

$$T_0 = T_1(t)/\exp^{(-t/\tau)} \quad \text{(Equation 8)}$$

In equation 8, $T_1$ and T(t) can be measured with the electronic thermometer 520, and the probe heat capacity can be assumed as already known in the product characteristics. Therefore, the heat source temperature (i.e., deep body temperature) can be theoretically calculated in calculation if the heat time constant of the measurement site is known.

However, the heat time constant of the measurement site is a parameter that differs among individuals due to personal physiological information (e.g., covering of fat and muscle at the measurement site).

The heat conduction model from the depth of the human body to the electronic thermometer 520 will be considered in a simplified manner as shown in the heat conduction model of FIG. 12(B). In other words, assuming from the heat source temperature $T_0$ towards the downstream side, the heat conductivity of the muscle portion is $k_1$ and the thickness thereof is $t_1$, the heat conductivity of the fat portion is $k_2$ and the thickness thereof is $t_2$, and the probe heat capacity is $C_1$, the following equation 9 is obtained.

$$\tau = 1/(C_1 \cdot (k_1 \cdot t_1 + k_2 \cdot t_2)) \quad \text{(Equation 9)}$$

Since the heat conductivity of the fat portion is very large compared to the heat conductivity of the muscle portion, $\tau$ is assumed to have a strong correlation with $(k_2 \cdot t_2)$.

Assuming $k_2$ (heat conductivity of fat portion) is a fixed value, $\tau$ can be experimentally estimated and the heat source temperature (deep temperature) can be accurately calculated in a short time if $t_2$ (thickness of fat portion) is known.

Therefore, in this example, the thickness of the subcutaneous fat at the armpit is measured with a device such as the body composition monitor with scale 100, and the measurement result is stored in the storage unit 527 of the electronic thermometer 520. The body temperature measurement program uses the same as the body temperature calculation parameter when the user measures the body temperature.

Figure 14:
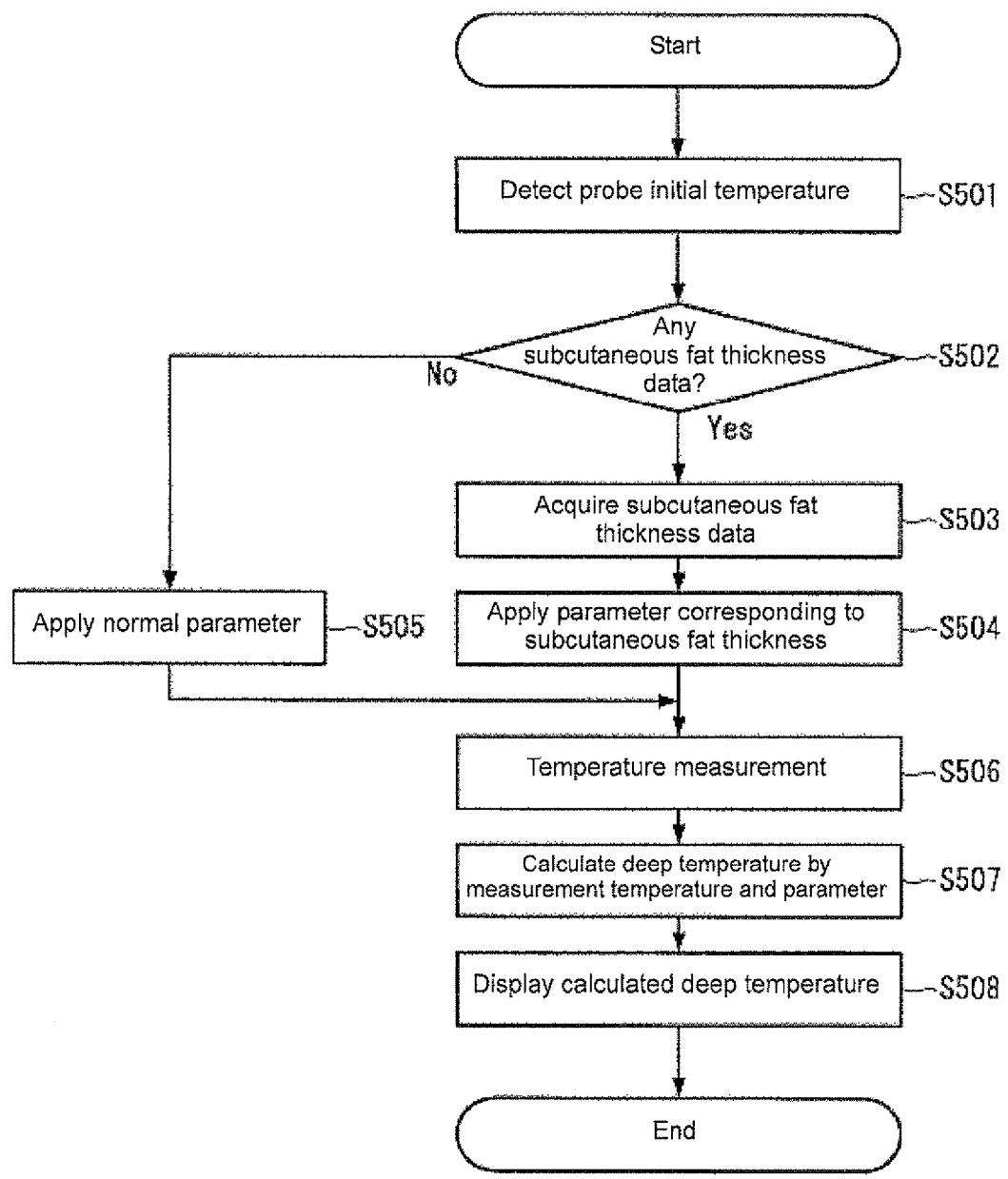
FIG. 14 is a flowchart showing the operation of the electronic thermometer of the fourth embodiment.

FIG. 14 is a flowchart showing the operation of the body temperature measurement in which the control unit 524 of the electronic thermometer 520 operates according to the body temperature measurement program. The user stores his/her subcutaneous fat thickness in the electronic thermometer 520 according to an appropriate method before performing the operation. This storage is carried out according to an appropriate method such as connecting the electronic thermometer 520 and the user terminal 510, acquiring the subcutaneous fat thickness of the user from the server 150 by screen operation of the user terminal 510 and writing to the storage unit 527 of the electronic thermometer 520, or manually inputting by the operation of the operation unit 526 of the electronic thermometer 520.

When the body temperature measurement starts by the operation of the operation unit 526, and the like, the control unit 524 detects the initial temperature of the temperature measuring unit 522 (step S501), and determines whether or not the subcutaneous fat thickness data is stored in the storage unit 527 (step S502). The subcutaneous fat thickness data to reference here may be appropriately set such as being dedicated to a fixed user by storing one data, or selecting the user with the operation unit 526 and using the subcutaneous fat thickness data of the selected user.

If the subcutaneous fat thickness data is present (step S502: Yes), the control unit 524 acquires the subcutaneous fat thickness data from the storage unit 527 (step S503), and applies the parameter corresponding to the subcutaneous fat thickness (step S504). The parameter may be appropriately obtained such as being calculated in advance from the subcutaneous fat thickness data, or being calculated from the subcutaneous fat thickness data each time.

If the subcutaneous fat thickness data is not present (step S502: No), the control unit 524 applies the normal parameter (step S505).

The control unit 524 executes the temperature measurement by the temperature measuring unit 522 (step S506), and calculates the deep temperature by the measurement temperature and the parameters (step S507). In this case, the deep temperature can be calculated with the parameter suited to the individual if the subcutaneous fat thickness data is present as it will be adopted.

The control unit 524 displays the calculated deep temperature on the display unit 523 (step S508), and terminates the process.

As described above, an electronic thermometer (electronic thermometer 520) including temperature measurement means (temperature measuring unit 522) for measuring the temperature of a living body as biological information acquiring means has a configuration in which the associated biological information acquiring means (control unit 524 that executes step S503) serving as the input means of the biological component information acquires the subcutaneous fat information (subcutaneous fat thickness) about the subcutaneous fat of the user, where the correction means (control unit 524 that executes step S504) acquires the subcutaneous fat information and corrects the parameter to that corresponding to the subcutaneous fat information, and the output means (display unit 523) outputs the body temperature calculated by the corrected parameter.

The electronic thermometer 520 can calculate the deep body temperature using the parameter corresponding to the characteristics of the user individual. In other words, the mode of temperature change until the surface temperature and the deep temperature become equilibrium differs between the user with thick subcutaneous fat and the user with thin subcutaneous fat, and thus the measurement error sometimes appears when calculated with the same parameter. However, the deep body temperature can be more accurately measured while avoiding such measurement error by using the parameter corresponding to the subcutaneous fat thickness of the user himself/herself.

Since the parameter corresponding to the fat portion having a very large heat conductivity than the muscle portion is used, this can be greatly put to use to enhance the measurement accuracy.

In the correspondence between the configuration of the present invention and the above described embodiment;

another device of the present invention corresponds to the MRI 10 of the embodiment, and similarly, a selection screen corresponds to the actual measurement data presence/absence inquiring screen 21;

selection means corresponds to the selection button 33 of the actual measurement data presence/absence inquiring screen 21;

display means corresponds to the specific individual measurement result display screen 40A;

a body composition measurement device and a biological information display device correspond to the body composition monitor with scale 100;

a biological information measurement device corresponds to the body composition monitor with scale 100 or the electronic thermometer 520;

input means corresponds to the communication unit 111;

storage means corresponds to the storage unit 112;

calculation means corresponds to the control unit 118 or the control unit 524;

measurement means corresponds to the control unit 118 that executes steps S8 to S11 or the control unit 524 that executes step S506;

target information creating means corresponds to the control unit 118 that executes step S23;

impedance measurement means corresponds to the impedance detection unit 120;

weight measurement means corresponds to the load detection unit 133;

a correction calculation method dedicated to the living body corresponds to the specific individual dedicated calculation equation A;

a living body categorized body composition calculation method corresponds to the general calculation equation B;

a selection step corresponds to step S3;

a measurement step corresponds to step S8;

a correction calculation method determining process corresponds to step S9;

a biological component reflecting calculation process corresponds to step S10;

a display step corresponds to step S11;

a general body composition calculation process corresponds to step S12; and a biological component information corresponds to a cross-sectional area, a site length, a subcutaneous fat percentage, a visceral fat percentage, and a contact impedance of the skin; but the present invention is not limited only to the configuration of the embodiments described above, and a great number of embodiments can be obtained.

INDUSTRIAL APPLICABILITY

The present invention can be used in the field of using a device for acquiring the body composition such as a body composition monitor and a body composition monitor with scale. For instance, the present invention can be used in various fields such as health management at home, health management in medical facilities such as hospitals, health management in health facilities such as health clubs, health management in rehabilitation facilities, health management in facilities such as a day care center or nursing home, and the like.

DESCRIPTION OF SYMBOLS

10 MRI
21 actual measurement data presence/absence inquiring screen
33 selection button
40A specific individual measurement result display screen
100 body composition monitor with scale
111 communication unit
112 storage unit
118 control unit
120 impedance detection unit
133 bad detection unit
A specific individual dedicated calculation equation
B general calculation equation

The invention claimed is:

1. A biological information measurement apparatus comprising:
a measurement device which acquires measurement value information of a living body;
a calculator which calculates biological information based on the measurement value information obtained by the measurement device; and
an input device which receives biological component information about a component of the living body measured in another device, together with date and time information at which the biological component information was received from the another device, wherein
the calculator is configured to:

determine whether or not the biological component information received from the another apparatus is effective based on the date and time information, calculate the biological information based on the biological component information and the measurement value information if the biological component information is determined as being effective, the biological information being calculated based on the biological component information and the measurement value information using the following equation:

$$f(\rho)=a_2 \cdot 1/\rho+b_2 \cdot W+c_2+S+d_2 \cdot e_2$$

calculate the biological information based on the measurement value information and not including the biological component information received from the another device if the biological component information is determined as being not effective, the biological information being calculated based on the measurement value information using the following equation:

$$f(\rho)=a_1 \cdot 1/\rho+b_1 \cdot W+c_1$$

wherein, $a_1$, $a_2$, $b_1$, $b_2$, $c_1$, $c_2$, $d_2$ and $e_2$ are predetermined constants, $\rho$ is a resistivity of the living body, S is a cross-sectional area of a body site, L is a site length of the body site, and W is a weight of the living body.

2. A body composition measurement apparatus according to claim 1, wherein
the measurement value information is an impedance or a weight of a living body; and
the biological information is a body composition.

3. The body composition measurement apparatus according to claim 1, further comprising:
a target information creating device which creates target information about the body composition based on the body composition component information, wherein
the target information creating device is configured to correct the target information based on the biological component information.

4. A biological information measurement method performed by a biological information measurement apparatus having: a measurement device which acquires measurement value information of a living body; and a calculation device which calculates biological information based on the measurement value information obtained by the measurement device; the biological information measurement method comprising:
receiving biological component information about a component of the living body measured in an another device, together with date and time information at which the biological component information was received from the another device, executing a determination of whether or not the biological component information received from the another apparatus is effective based on the date and time information, executing a biological component reflecting calculation if the biological component information is determined as being effective, which calculates the biological information based on the biological component information and the measurement value information, the biological information being calculated based on the biological component information and the measurement value information using the following equation:

$$f(\rho)=a_2 \cdot 1/\rho+b_2 \cdot W+c_2+S+d_2 \cdot e_2$$

executing a general body composition calculation if the biological component information is determined as being not effective, which calculates the general body composition based on the measurement value information and not including the biological component information received from the another device, the general body composition being calculated based on the measurement value information using the following equation:

$$f(\rho)=a_1 \cdot 1/\rho+b_1 \cdot W+c_1$$

wherein, $a_1$, $a_2$, $b_1$, $b_2$, $c_1$, $c_2$, $d_2$ and $e_2$ are predetermined constants, $\rho$ is a resistivity of the living body, S is a cross-sectional area of a body site, L is a site length of the body site, and W is a weight of the living body.

5. The body composition measurement apparatus according to claim 1, wherein
the another device is at least one device that acquires the body composition component information selected from a group of a Magnetic Resonance Imaging (MRI) device, a Computed Tomography (CT) device, or a Dual Energy X-Ray Absorptiometry (DEXA) device.

6. The biological information measurement method according to claim 4, wherein
the another device is at least one device that acquires the body composition component information selected from a group of a Magnetic Resonance Imaging (MRI) device, a Computed Tomography (CT) device, or a Dual Energy X-Ray Absorptiometry (DEXA) device.

7. The body composition measurement apparatus according to claim 1, wherein the constants $a_1$, $b_1$ and $c_1$ are determined based on height, age and sex of the living body.

8. The biological information measurement method according to claim 4, wherein the constants $a_1$, $b_1$ and $c_1$ are determined based on height, age and sex of the living body.

* * * * *